United States Patent
Colletti et al.

(10) Patent No.: US 10,307,378 B2
(45) Date of Patent: Jun. 4, 2019

(54) DIESTER AND TRIESTER BASED LOW MOLECULAR WEIGHT, BIODEGRADEABLE CATIONIC LIPIDS FOR OLIGONUCLEOTIDE DELIVERY

(71) Applicant: SIRNA THERAPEUTICS, INC., Cambridge, MA (US)

(72) Inventors: Steven L. Colletti, West Point, PA (US); Matthew G. Stanton, West Point, PA (US)

(73) Assignee: SIRNA THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/827,162

(22) Filed: Nov. 30, 2017

(65) Prior Publication Data

US 2018/0193279 A1    Jul. 12, 2018

Related U.S. Application Data

(63) Continuation of application No. 15/198,271, filed on Jun. 30, 2016, now Pat. No. 9,861,589, which is a continuation of application No. 14/395,267, filed as application No. PCT/US2013/036682 on Apr. 16, 2013, now Pat. No. 9,402,816.

(60) Provisional application No. 61/635,494, filed on Apr. 19, 2012.

(51) Int. Cl.
| | |
|---|---|
| A61K 9/51 | (2006.01) |
| C07F 7/18 | (2006.01) |
| A61K 47/60 | (2017.01) |
| C12N 15/11 | (2006.01) |
| A61K 31/713 | (2006.01) |
| C07C 229/12 | (2006.01) |
| C07C 229/28 | (2006.01) |
| C07C 229/30 | (2006.01) |
| C12N 15/113 | (2010.01) |

(52) U.S. Cl.
CPC .............. *A61K 9/5123* (2013.01); *A61K 9/51* (2013.01); *A61K 9/5146* (2013.01); *A61K 31/713* (2013.01); *A61K 47/60* (2017.08); *C07C 229/12* (2013.01); *C07C 229/28* (2013.01); *C07C 229/30* (2013.01); *C07F 7/1804* (2013.01); *C12N 15/111* (2013.01); *C12N 15/113* (2013.01); *C07C 2601/02* (2017.05); *C12N 2310/14* (2013.01); *C12N 2320/32* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 9,061,063 | B2 | 6/2015 | Maier et al. |
| 9,402,816 | B2 | 8/2016 | Colletti et al. |
| 2006/0083780 | A1 | 4/2006 | Heyes et al. |
| 2006/0240554 | A1 | 10/2006 | Chen et al. |
| 2008/0020058 | A1 | 1/2008 | Chen et al. |
| 2009/0263407 | A1 | 10/2009 | Dande et al. |
| 2009/0285881 | A1 | 11/2009 | Dande |
| 2012/0027803 | A1 | 2/2012 | Manoharan et al. |
| 2015/0005363 | A1 | 1/2015 | Ansell et al. |

FOREIGN PATENT DOCUMENTS

| | | | | |
|---|---|---|---|---|
| WO | 2009/086558 A1 | 7/2009 | | |
| WO | 2009/127060 A1 | 10/2009 | | |
| WO | 2009/132131 A1 | 10/2009 | | |
| WO | 2010/042877 A1 | 4/2010 | | |
| WO | 2010/054384 A1 | 5/2010 | | |
| WO | 2010/054401 A1 | 5/2010 | | |
| WO | 2010/054405 A1 | 5/2010 | | |
| WO | 2010/054406 A1 | 5/2010 | | |
| WO | WO 2011/141703 A1 * | 11/2011 | ........... | C12N 15/113 |
| WO | WO 2011/141704 A1 * | 11/2011 | ........... | C07C 217/28 |
| WO | 2011/153493 A2 | 12/2011 | | |
| WO | 2012/040184 A2 | 3/2012 | | |
| WO | 2012/054365 A2 | 4/2012 | | |

OTHER PUBLICATIONS

Chance et al., "Gas-liquid chromatography-mass spectrometry of hydroxy fatty acids as their methyl esters tert.-butyldimethylsilyl ethers", Journal of Chromatography A 793:91-98 (1998).
Database CAPLUS in STN Accession No. 1997:808125, "Chance et al., Journal of Chromatography A 793(1):91-98 (1998)". (Abstract).

* cited by examiner

*Primary Examiner* — Brian J Davis
(74) *Attorney, Agent, or Firm* — Nixon Peabody LLP

(57) ABSTRACT

The instant invention provides for novel cationic lipids of Formula A that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain coupled with inclusion of hydrolysable functionality in the lipid chains to enhance the efficiency and tolerability of in vivo delivery of siRNA.

9 Claims, No Drawings

Specification includes a Sequence Listing.

SEQUENCE LISTING

```
<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: ribonucleotide modified or unmodified as
      described for this sequence
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(1)
<223> OTHER INFORMATION: 2' deoxy
<220> FEATURE:
<221> NAME/KEY: misc_feature
<222> LOCATION: (2)..(2)
<223> OTHER INFORMATION: 2' fluoro
<220> FEATURE:
<221> NAME/KEY: misc_feature
<222> LOCATION: (3)..(6)
<223> OTHER INFORMATION: 2' deoxy
<220> FEATURE:
<221> NAME/KEY: misc_feature
<222> LOCATION: (7)..(8)
<223> OTHER INFORMATION: 2' fluoro
<220> FEATURE:
<221> NAME/KEY: misc_feature
<222> LOCATION: (9)..(9)
<223> OTHER INFORMATION: 2' deoxy
<220> FEATURE:
<221> NAME/KEY: misc_feature
<222> LOCATION: (10)..(10)
<223> OTHER INFORMATION: 2' fluoro
<220> FEATURE:
<221> NAME/KEY: misc_feature
<222> LOCATION: (11)..(17)
<223> OTHER INFORMATION: 2' deoxy
<220> FEATURE:
<221> NAME/KEY: misc_feature
<222> LOCATION: (18)..(18)
<223> OTHER INFORMATION: 2' fluoro
<220> FEATURE:
<221> NAME/KEY: misc_feature
<222> LOCATION: (19)..(21)
<223> OTHER INFORMATION: 2' deoxy
<220> FEATURE:
```

```
<221> NAME/KEY: misc_feature
<222> LOCATION: (21)..(21)
<223> OTHER INFORMATION: inverted deoxy abasic

<400> SEQUENCE: 1
auaaggcuau gaagagauat t                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (4)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(11)
<223> OTHER INFORMATION: 2' fluoro
<220> FEATURE:
<221> NAME/KEY: misc_feature
<222> LOCATION: (12)..(13)
<223> OTHER INFORMATION: 2' O-methyl
<220> FEATURE:
<221> NAME/KEY: misc_feature
<222> LOCATION: (14)..(17)
<223> OTHER INFORMATION: 2' fluoro
<220> FEATURE:
<221> NAME/KEY: misc_feature
<222> LOCATION: (18)..(18)
<223> OTHER INFORMATION: 2' O-methyl
<220> FEATURE:
<221> NAME/KEY: misc_feature
<222> LOCATION: (19)..(19)
<223> OTHER INFORMATION: 2' fluoro
<220> FEATURE:
<221> NAME/KEY: misc_feature
<222> LOCATION: (20)..(21)
<223> OTHER INFORMATION: 2' O-methyl

<400> SEQUENCE: 2
uaucucuuca uagccuuauu u                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(4)
<223> OTHER INFORMATION: 2' O-methyl
<220> FEATURE:
<221> NAME/KEY: misc_feature
<222> LOCATION: (5)..(6)
<223> OTHER INFORMATION: 2' fluoro
<220> FEATURE:
<221> NAME/KEY: misc_feature
<222> LOCATION: (7)..(7)
<223> OTHER INFORMATION: 2' O-methyl
```

-continued

```
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(14)
<223> OTHER INFORMATION: 2' O-methyl
<220> FEATURE:
<221> NAME/KEY: misc_feature
<222> LOCATION: (15)..(18)
<223> OTHER INFORMATION: 2' fluoro
<220> FEATURE:
<221> NAME/KEY: misc_feature
<222> LOCATION: (19)..(19)
<223> OTHER INFORMATION: 2' O-methyl
<220> FEATURE:
<221> NAME/KEY: misc_feature
<222> LOCATION: (20)..(21)
<223> OTHER INFORMATION: 2' deoxy
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (21)..(21)
<223> OTHER INFORMATION: inverted deoxy abasic

<400> SEQUENCE: 3
cuuuaacaau uccugaaaut t                                           21

<210> SEQ ID NO 4
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: ribose
<220> FEATURE:
<221> NAME/KEY: misc_feature
<222> LOCATION: (1)..(4)
<223> OTHER INFORMATION: phophorothioate linkage
<220> FEATURE:
<221> NAME/KEY: misc_feature
<222> LOCATION: (4)..(5)
<223> OTHER INFORMATION: 2' O-methyl
<220> FEATURE:
<221> NAME/KEY: misc_feature
<222> LOCATION: (6)..(10)
<223> OTHER INFORMATION: 2' fluoro
<220> FEATURE:
<221> NAME/KEY: misc_feature
<222> LOCATION: (11)..(12)
<223> OTHER INFORMATION: 2' O-methyl
<220> FEATURE:
<221> NAME/KEY: misc_feature
<222> LOCATION: (13)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(19)
<223> OTHER INFORMATION: 2' fluoro
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (20)..(21)
```

```
<223> OTHER INFORMATION: 2' O-methyl

<400> SEQUENCE: 4
auuucaggaa uuguuaaagu u                                              21

<210> SEQ ID NO 5
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(2)
<223> OTHER INFORMATION: ribose
<220> FEATURE:
<221> NAME/KEY: misc_feature
<222> LOCATION: (3)..(3)
<223> OTHER INFORMATION: 2' O-methyl
<220> FEATURE:
<221> NAME/KEY: misc_feature
<222> LOCATION: (4)..(5)
<223> OTHER INFORMATION: ribose
<220> FEATURE:
<221> NAME/KEY: misc_feature
<222> LOCATION: (6)..(8)
<223> OTHER INFORMATION: 2' O-methyl
<220> FEATURE:
<221> NAME/KEY: misc_feature
<222> LOCATION: (9)..(10)
<223> OTHER INFORMATION: ribose
<220> FEATURE:
<221> NAME/KEY: misc_feature
<222> LOCATION: (11)..(12)
<223> OTHER INFORMATION: 2' O-methyl
<220> FEATURE:
<221> NAME/KEY: misc_feature
<222> LOCATION: (13)..(14)
<223> OTHER INFORMATION: ribose
<220> FEATURE:
<221> NAME/KEY: misc_feature
<222> LOCATION: (15)..(21)
<223> OTHER INFORMATION: 2' O-methyl
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (21)..(21)
<223> OTHER INFORMATION: inverted deoxy abasic

<400> SEQUENCE: 5 cguuggauu gauucgaaau u                                               21

<210> SEQ ID NO 6
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: 2' fluoro
<220> FEATURE:
<221> NAME/KEY: misc_feature
<222> LOCATION: (5)..(6)
<223> OTHER INFORMATION: 2' O-methyl
<220> FEATURE:
<221> NAME/KEY: misc_feature
```

```
<222> LOCATION: (7)..(8)
<223> OTHER INFORMATION: 2' fluoro
<220> FEATURE:
<221> NAME/KEY: misc_feature
<222> LOCATION: (9)..(9)
<223> OTHER INFORMATION: ribose
<220> FEATURE:
<221> NAME/KEY: misc_feature
<222> LOCATION: (10)..(10)
<223> OTHER INFORMATION: 2' fluoro
<220> FEATURE:
<221> NAME/KEY: misc_feature
<222> LOCATION: (11)..(11)
<223> OTHER INFORMATION: 2' O-methyl
<220> FEATURE:
<221> NAME/KEY: misc_feature
<222> LOCATION: (12)..(12)
<223> OTHER INFORMATION: ribose
<220> FEATURE:
<221> NAME/KEY: misc_feature
<222> LOCATION: (13)..(13)
<223> OTHER INFORMATION: 2' O-methyl
<220> FEATURE:
<221> NAME/KEY: misc_feature
<222> LOCATION: (14)..(14)
<223> OTHER INFORMATION: 2' fluoro
<220> FEATURE:
<221> NAME/KEY: misc_feature
<222> LOCATION: (15)..(15)
<223> OTHER INFORMATION: ribose
<220> FEATURE:
<221> NAME/KEY: misc_feature
<222> LOCATION: (16)..(16)
<223> OTHER INFORMATION: 2' fluoro
<220> FEATURE:
<221> NAME/KEY: misc_feature
<222> LOCATION: (17)..(17)
<223> OTHER INFORMATION: 2' O-methyl
<220> FEATURE:
<221> NAME/KEY: misc_feature
<222> LOCATION: (18)..(18)
<223> OTHER INFORMATION: 2' fluoro
<220> FEATURE:
<221> NAME/KEY: misc_feature
<222> LOCATION: (19)..(19)
<223> OTHER INFORMATION: ribose
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature
<222> LOCATION: (20)..(21)
<223> OTHER INFORMATION: phophorothioate linkage

<400> SEQUENCE: 6
uuucgaauca auccaacagu u                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(1)
<223> OTHER INFORMATION: 2' fluoro
<220> FEATURE:
<221> NAME/KEY: misc_feature
<222> LOCATION: (2)..(2)
<223> OTHER INFORMATION: 2' deoxy
<220> FEATURE:
```

<221> NAME/KEY: misc_feature
<222> LOCATION: (3)..(4)
<223> OTHER INFORMATION: 2' fluoro
<220> FEATURE:
<221> NAME/KEY: misc_feature
<222> LOCATION: (5)..(5)
<223> OTHER INFORMATION: 2' O-methyl
<220> FEATURE:
<221> NAME/KEY: misc_feature
<222> LOCATION: (6)..(7)
<223> OTHER INFORMATION: 2' deoxy
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(11)
<223> OTHER INFORMATION: ribose
<220> FEATURE:
<221> NAME/KEY: misc_feature
<222> LOCATION: (12)..(14)
<223> OTHER INFORMATION: 2' deoxy
<220> FEATURE:
<221> NAME/KEY: misc_feature
<222> LOCATION: (15)..(15)
<223> OTHER INFORMATION: ribose
<220> FEATURE:
<221> NAME/KEY: misc_feature
<222> LOCATION: (16)..(16)
<223> OTHER INFORMATION: 2' deoxy
<220> FEATURE:
<221> NAME/KEY: misc_feature
<222> LOCATION: (17)..(17)
<223> OTHER INFORMATION: ribose
<220> FEATURE:
<221> NAME/KEY: misc_feature
<222> LOCATION: (18)..(18)
<223> OTHER INFORMATION: 2' O-methyl
<220> FEATURE:
<221> NAME/KEY: misc_feature
<222> LOCATION: (19)..(19)
<223> OTHER INFORMATION: 2' deoxy
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature
<222> LOCATION: (20)..(21)
<223> OTHER INFORMATION: phophorothioate linkage
<220> FEATURE:
<221> NAME/KEY: misc_feature
<222> LOCATION: (21)..(21)
<223> OTHER INFORMATION: inverted deoxy abasic

<400> SEQUENCE: 7
acgacuaguu caguugcuuu u                                               21

<210> SEQ ID NO 8
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2' fluoro
<220> FEATURE:
<221> NAME/KEY: misc_feature
<222> LOCATION: (3)..(4)
<223> OTHER INFORMATION: 2' O-methyl

```
<220> FEATURE:
<221> NAME/KEY: misc_feature
<222> LOCATION: (5)..(5)
<223> OTHER INFORMATION: 2' fluoro
<220> FEATURE:
<221> NAME/KEY: misc_feature
<222> LOCATION: (6)..(6)
<223> OTHER INFORMATION: ribose
<220> FEATURE:
<221> NAME/KEY: misc_feature
<222> LOCATION: (7)..(7)
<223> OTHER INFORMATION: 2' fluoro
<220> FEATURE:
<221> NAME/KEY: misc_feature
<222> LOCATION: (8)..(11)
<223> OTHER INFORMATION: 2' O-methyl
<220> FEATURE:
<221> NAME/KEY: misc_feature
<222> LOCATION: (12)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
<222> LOCATION: (16)..(17)
<223> OTHER INFORMATION: ribose
<220> FEATURE:
<221> NAME/KEY: misc_feature
<222> LOCATION: (18)..(21)
<223> OTHER INFORMATION: 2' O-methyl
<220> FEATURE:
<221> NAME/KEY: misc_feature
<222> LOCATION: (20)..(21)
<223> OTHER INFORMATION: phophorothioate linkage

<400> SEQUENCE: 8
aagcaacuga acuagucguu u                                              21

<210> SEQ ID NO 9
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: inverted deoxy abasic
<220> FEATURE:
<221> NAME/KEY: misc_feature
<222> LOCATION: (1)..(1)
<223> OTHER INFORMATION: 2' fluoro
<220> FEATURE:
<221> NAME/KEY: misc_feature
<222> LOCATION: (2)..(2)
<223> OTHER INFORMATION: 2' deoxy
<220> FEATURE:
<221> NAME/KEY: misc_feature
<222> LOCATION: (3)..(4)
<223> OTHER INFORMATION: 2' fluoro
<220> FEATURE:
<221> NAME/KEY: misc_feature
<222> LOCATION: (6)..(7)
<223> OTHER INFORMATION: 2' deoxy
<220> FEATURE:
<221> NAME/KEY: misc_feature
<222> LOCATION: (8)..(9)
<223> OTHER INFORMATION: 2' fluoro
<220> FEATURE:
<221> NAME/KEY: misc_feature
<222> LOCATION: (10)..(10)
<223> OTHER INFORMATION: 2' O-methyl
<220> FEATURE:
<221> NAME/KEY: misc_feature
<222> LOCATION: (11)..(11)
```

-continued

```
<223> OTHER INFORMATION: ribose
<220> FEATURE:
<221> NAME/KEY: misc_feature
<222> LOCATION: (12)..(14)
<223> OTHER INFORMATION: 2' deoxy
<220> FEATURE:
<221> NAME/KEY: misc_feature
<222> LOCATION: (15)..(15)
<223> OTHER INFORMATION: ribose
<220> FEATURE:
<221> NAME/KEY: misc_feature
<222> LOCATION: (16)..(16)
<223> OTHER INFORMATION: ribose
<220> FEATURE:
<221> NAME/KEY: misc_feature
<222> LOCATION: (17)..(17)
<223> OTHER INFORMATION: ribose
<220> FEATURE:
<221> NAME/KEY: misc_feature
<222> LOCATION: (18)..(18)
<223> OTHER INFORMATION: 2' O-methyl
<220> FEATURE:
<221> NAME/KEY: misc_feature
<222> LOCATION: (19)..(19)
<223> OTHER INFORMATION: 2' deoxy
<220> FEATURE:
<221> NAME/KEY: misc_feature
<222> LOCATION: (20)..(21)
<223> OTHER INFORMATION: 2' O-methyl
<220> FEATURE:
<221> NAME/KEY: misc_feature
<222> LOCATION: (21)..(21)
<223> OTHER INFORMATION: inverted deoxy abasic

<400> SEQUENCE: 9
acgacuaguu caguugcuuu u                                              21

<210> SEQ ID NO 10
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: 2' fluoro
<220> FEATURE:
<221> NAME/KEY: misc_feature
<222> LOCATION: (3)..(4)
<223> OTHER INFORMATION: 2' O-methyl
<220> FEATURE:
<221> NAME/KEY: misc_feature
<222> LOCATION: (5)..(5)
<223> OTHER INFORMATION: 2' fluoro
<220> FEATURE:
<221> NAME/KEY: misc_feature
<222> LOCATION: (6)..(6)
<223> OTHER INFORMATION: ribose
<220> FEATURE:
<221> NAME/KEY: misc_feature
<222> LOCATION: (7)..(7)
<223> OTHER INFORMATION: 2' fluoro
<220> FEATURE:
<221> NAME/KEY: misc_feature
<222> LOCATION: (8)..(11)
<223> OTHER INFORMATION: 2' O-methyl
<220> FEATURE:
<221> NAME/KEY: misc_feature
<222> LOCATION: (12)..(14)
<223> OTHER INFORMATION: 2' fluoro
<220> FEATURE:
<221> NAME/KEY: misc_feature
<222> LOCATION: (15)..(15)
<223> OTHER INFORMATION: 2' O-methyl
<220> FEATURE:
<221> NAME/KEY: misc_feature
```

```
<222> LOCATION: (16)..(17)
<223> OTHER INFORMATION: ribose
<220> FEATURE:
<221> NAME/KEY: misc_feature
<222> LOCATION: (18)..(21)
<223> OTHER INFORMATION: 2' O-methyl

<400> SEQUENCE: 10
aagcaacuga acuagucguu u                                                   21

<210> SEQ ID NO 11
<211> LENGTH: 52
<212> TYPE: DNA
<213> ORGANISM: Artificial Sequence
<220> FEATURE:
<223> OTHER INFORMATION: Synthetic

<400> SEQUENCE: 11
gtcgtatcca gtgcagggtc cgaggtattc gcactggata cgacctttaa ca                 52

<210> SEQ ID NO 12
<211> LENGTH: 22
<212> TYPE: DNA
<213> ORGANISM: Artificial Sequence
<220> FEATURE:
<223> OTHER INFORMATION: Synthetic

<400> SEQUENCE: 12
ggcgcgaaat ttcaggaatt gt                                                  22

<210> SEQ ID NO 13
<211> LENGTH: 21
<212> TYPE: DNA
<213> ORGANISM: Artificial Sequence
<220> FEATURE:
<223> OTHER INFORMATION: Synthetic

<400> SEQUENCE: 13
cactggatac gacctttaac a                                                   21

<210> SEQ ID NO 14
<211> LENGTH: 15
<212> TYPE: DNA
<213> ORGANISM: Artificial Sequence
<220> FEATURE:
<223> OTHER INFORMATION: Synthetic

<400> SEQUENCE: 14
agtgcagggt ccgag                                                          15
```

DIESTER AND TRIESTER BASED LOW MOLECULAR WEIGHT, BIODEGRADEABLE CATIONIC LIPIDS FOR OLIGONUCLEOTIDE DELIVERY

CROSS REFERENCE TO RELATED APPLICATIONS

This application is a continuation of U.S. application Ser. No. 15/198,271 filed Jun. 30, 2016, which application is a continuation of U.S. application Ser. No. 14/395,267 filed Oct. 17, 2014, now U.S. Pat. No. 9,402,816 issued on Aug. 2, 2016, which is a 35 U.S.C. § 371 National Phase Entry Application of International Application No. PCT/US2013/036682 filed Apr. 16, 2013, which designates the U.S., and which claims benefit under 35 U.S.C. § 119(e) of the U.S. Provisional Application No. 61/635,494, filed Apr. 19, 2012, the content of which is incorporated herein by reference in its entirety.

SEQUENCE LISTING

The sequence listing of the present application has been submitted electronically via EFS-Web as an ASCII formatted sequence listing with a file name "23222WOPCTSEQ", creation date of Jun. 29, 2016 and a size of 11,409 bytes. The sequence listing submitted via EFS-Web is part of the specification and is herein incorporated by reference in its entirety.

BACKGROUND OF THE INVENTION

The present invention relates to novel diester and triester cationic lipids that can be used in combination with other lipid components such as cholesterol and PEG-lipids to form lipid nanoparticles with oligonucleotides, to facilitate the cellular uptake and endosomal escape, and to knockdown target mRNA both in vitro and in vivo.

Cationic lipids and the use of cationic lipids in lipid nanoparticles for the delivery of oligonucleotides, in particular siRNA and miRNA, have been previously disclosed. Lipid nanoparticles and use of lipid nanoparticles for the delivery of oligonucleotides, in particular siRNA and miRNA, have been previously disclosed. Oligonucleotides (including siRNA and miRNA) and the synthesis of oligonucleotides have been previously disclosed. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405, WO2010/054406 and WO2011/153493). See also Semple S. C. et al., Rational design of cationic lipids for siRNA delivery, *Nature Biotechnology,* 2010, 28, 172-176.

Other cationic lipids are disclosed in the following patent applications: US 2009/0263407, US 2009/0285881, US 2010/0055168, US 2010/0055169, US 2010/0063135, US 2010/0076055, US 2010/0099738, US 2010/0104629, WO2010/088537, WO2010/144740, US2010/0324120, U.S. Pat. No. 8,034,376, WO2011/143230, WO2011/000106, US2011/0117125, US2011/0256175, WO2011/141703, WO2011/141704 and WO2011/141705.

Traditional cationic lipids such as CLinDMA and DLinDMA have been used for siRNA delivery to the liver but suffer from non-optimal delivery efficiency along with liver toxicity at higher doses. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain coupled with inclusion of hydrolysable functionality in the lipid chains to enhance the efficiency and tolerability of in vivo delivery of siRNA.

SUMMARY OF THE INVENTION

The instant invention provides for novel cationic lipids of Formula A that can be used in combination with other lipid components such as cholesterol and PEG-lipids to form lipid nanoparticles with oligonucleotides. It is an object of the instant invention to provide a cationic lipid scaffold that demonstrates enhanced efficacy along with lower liver toxicity as a result of lower lipid levels in the liver. The present invention employs low molecular weight cationic lipids with one short lipid chain coupled with inclusion of hydrolysable functionality in the lipid chains to enhance the efficiency and tolerability of in vivo delivery of siRNA.

DETAILED DESCRIPTION OF THE INVENTION

The various aspects and embodiments of the invention are directed to novel cationic lipids useful in lipid nanoparticles to deliver oligonucleotides, in particular, siRNA and miRNA, to any target gene. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405, WO2010/054406 and WO2011/153493). See also Semple S. C. et al., Rational design of cationic lipids for siRNA delivery, *Nature Biotechnology,* 2010, 28, 172-176.

The cationic lipids of the instant invention are useful components in a lipid nanoparticle for the delivery of oligonucleotides, specifically siRNA and miRNA.

In a first embodiment of this invention, the cationic lipids are illustrated by Formula A:

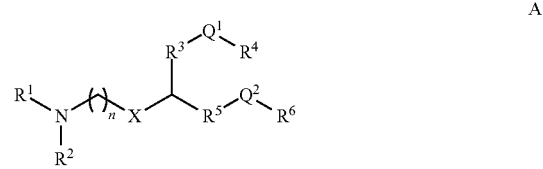

A wherein:

$R^1$ and $R^2$ are each independently selected from the group consisting of H, $(C_1-C_6)$alkyl, heterocyclyl, and polyamine, wherein said alkyl, heterocyclyl and polyamine are optionally substituted with one to three R'; or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three R';

$R^3$ is selected from the group consisting of $(C_4-C_{20})$alkyl and $(C_4-C_{20})$alkenyl, said alkyl or alkenyl is optionally substituted with one to three R';

$R^4$ is selected from the group consisting of $(C_1-C_{16})$alkyl and $(C_2-C_{16})$alkenyl, said alkyl or alkenyl is optionally substituted with one to three R';

$R^5$ is selected from the group consisting of $(C_4-C_8)$alkyl and $(C_4-C_8)$alkenyl, said alkyl or alkenyl is optionally substituted with one to three R';

$R^6$ is $(C_1-C_2)$alkyl, said alkyl is optionally substituted with one to three R';

$Q^1$ and $Q^2$ are each, independently, selected from the group consisting of a bond, —OC(O)—, —C(O)O—, —SC(O)—, —C(O)S—, —OC(S)—, —S—S—, —C(R")=N—, —N=C(R")—, —C(R")=N—O—, —O—N=C(R")—, —C(O)(NR")—, —N(R")C(O)—, C(S)(NR")—, —N(R")C(O)—, —N(R")C(O)N(R")—, —OC(O)O—, OSi(R")$_2$O—, —C(O)(CR"$_2$)C(O)O— and —OC(O)(CR"$_2$)C(O)—), with the proviso that when either $Q^1$ or $Q^2$ is a bond then the other is not a bond;

X is selected from the group consisting of —OC(O)—, —C(O)O—, —SC(O)—, —C(O)S—, —OC(S)—, —S—S—, —C(R")=N—, —N=C(R")—, —C(R")=N—O—, —O—N=C(R")—, —C(O)(NR")—, —N(R")C(O)—, C(S)(NR")—, —N(R")C(O)—, —N(R")C(O)N(R")—, —OC(O)O—, OSi(R")$_2$O—, —C(O)(CR"$_2$)C(O)O— and —OC(O)(CR"$_2$)C(O)—), each occurrence of R' is independently selected from the group consisting of halogen, R", OR", SR", CN, CO$_2$R" and CON(R")$_2$;

each occurrence of R" is independently selected from the group consisting of H and $(C_1-C_6)$alkyl, wherein said alkyl is optionally substituted with halogen and OH; and n is 1, 2, 3, 4 or 5;

or a pharmaceutically acceptable salt or stereoisomer thereof.

In a second embodiment, the invention features a compound having Formula A as described above, wherein:

$R^1$ and $R^2$ are each methyl;

n is 3;

$R^3$ is selected from $(C_4-C_{20})$alkyl and $(C_4-C_{20})$alkenyl, said alkyl or alkenyl is optionally substituted with one to three R';

$R^4$ is selected from $(C_1-C_{16})$alkyl and $(C_2-C_{16})$alkenyl, said alkyl or alkenyl is optionally substituted with one to three substituents selected from R';

$R^5$ is selected from $(C_4-C_8)$alkyl and $(C_4-C_8)$alkenyl, said alkyl or alkenyl is optionally substituted with one to three R';

$R^6$ is $(C_1-C_2)$alkyl, said alkyl is optionally substituted with one to three R';

$Q^1$ and $Q^2$ are each, independently, a bond or —C(O)O—, with the proviso that when either $Q^1$ or $Q^2$ is a bond then the other is not a bond;

X is —C(O)O—; and

R' is as defined above;

or a pharmaceutically acceptable salt or stereoisomer thereof.

Specific embodiments of the cationic lipids disclosed herein are:

methyl (9Z)-19-{[4-(dimethylamino)butanoyl]oxy}octacos-9-enoate (Compound 1);

methyl 8-[2-(9-{[4-(dimethylamino)butanoyl]oxy}octadecyl)cyclopropyl]octanoate (Compound 2);

methyl (9Z)-19-{[4-(dimethylamino)butanoyl]oxy}heptacos-9-enoate (Compound 3);

methyl (9Z)-19-{[4-(dimethylamino)butanoyl]oxy}hexacos-9-enoate (Compound 4);

methyl (9Z)-19-{[4-(dimethylamino)butanoyl]oxy}pentacos-9-enoate (Compound 5);

methyl (9Z)-21-{[4-(dimethylamino)butanoyl]oxy}triacont-9-enoate (Compound 6);

methyl (9Z)-21-{[4-(dimethylamino)butanoyl]oxy}nonacos-9-enoate (Compound 7);

methyl (9Z)-21-{[4-(dimethylamino)butanoyl]oxy}octacos-9-enoate (Compound 8);

methyl (9Z)-21-{[4-(dimethylamino)butanoyl]oxy}heptacos-9-enoate (Compound 9);

methyl (11Z)-19-{[4-(dimethylamino)butanoyl]oxy}octacos-11-enoate (Compound 10);

methyl (7Z)-19-{[4-(dimethylamino)butanoyl]oxy}octacos-7-enoate (Compound 11);

methyl 8-[2-(9-{[4-(dimethylamino)butanoyl]oxy}heptadecyl)cyclopropyl]octanoate (Compound 12);

methyl 8-[2-(9-{[4-(dimethylamino)butanoyl]oxy}hexadecyl)cyclopropyl]octanoate (Compound 13);

methyl 8-[2-(9-{[4-(dimethylamino)butanoyl]oxy}pentadecyl)cyclopropyl]octanoate (Compound 14);

methyl 8-[2-(11-{[4-(dimethylamino)butanoyl]oxy}icosyl)cyclopropyl]octanoate (Compound 15);

methyl 8-[2-(11-{[4-(dimethylamino)butanoyl]oxy}nonadecyl)cyclopropyl]octanoate (Compound 16);

methyl 8-{2-[11-(dimethylamino)octadecyl]cyclopropyl}octanoate (Compound 17);

methyl 8-[2-(11-{[4-(dimethylamino)butanoyl]oxy}octadecyl)cyclopropyl]octanoate (Compound 18);

methyl 10-[2-(7-{[4-(dimethylamino)butanoyl]oxy}hexadecyl)cyclopropyl]decanoate (Compound 19);

methyl 6-[2-(11-{[4-(dimethylamino)butanoyl]oxy}icosyl)cyclopropyl]hexanoate (Compound 20);

ethyl (7Z)-17-{[4-(dimethylamino)butanoyl]oxy}hexacos-7-enoate (Compound 21);

ethyl 6-[2-(9-{[4-(dimethylamino)butanoyl]oxy}octadecyl)cyclopropyl]hexanoate (Compound 22);

(2Z)-non-2-en-1-yl 10-{[4-(dimethylamino)butanoyl]oxy}nonadecanoate (Compound 23);

(2-hexylcyclopropyl)methyl 10-{[4-(dimethylamino)butanoyl]oxy}nonadecanoate (Compound 24);

(2Z)-undec-2-en-1-yl 8-{[4-(dimethylamino)butanoyl]oxy}heptadecanoate (Compound 25);

(2Z)-hept-2-en-1-yl 12-{[4-(dimethylamino)butanoyl]oxy}henicosanoate (Compound 26);

(2-octylcyclopropyl)methyl 8-{[4-(dimethylamino)butanoyl]oxy}heptadecanoate (Compound 27);

(2-butylcyclopropyl)methyl 12-{[4-(dimethylamino)butanoyl]oxy}henicosanoate (Compound 28);

methyl (19Z,22Z)-9-{[4-(dimethylamino)butanoyl]oxy}octacosa-19,22-dienoate (Compound 29);

ethyl (18Z,21Z)-8-{[4-(dimethylamino)butanoyl]oxy}heptacosa-18,21-dienoate (Compound 30);

methyl 9-{[4-(dimethylamino)butanoyl]oxy}-16-(2-octylcyclopropyl)hexadecanoate (Compound 31);

ethyl 8-{[4-(dimethylamino)butanoyl]oxy}-15-(2-octylcyclopropyl)pentadecanoate (Compound 32);

dimethyl (9Z)-19-{[4-(dimethylamino)butanoyl]oxy}heptacos-9-enedioate (Compound 33); and 1-methyl 18-[(2Z)-non-2-en-1-yl] 9-{[4-(dimethylamino)butanoyl]oxy}octadecanedioate (Compound 34);

or a pharmaceutically acceptable salt or stereoisomer thereof.

In another embodiment, the cationic lipids disclosed are useful in the preparation of lipid nanoparticles.

In another embodiment, the cationic lipids disclosed are useful components in a lipid nanoparticle for the delivery of oligonucleotides.

In another embodiment, the cationic lipids disclosed are useful components in a lipid nanoparticle for the delivery of siRNA and miRNA.

In another embodiment, the cationic lipids disclosed are useful components in a lipid nanoparticle for the delivery of siRNA.

The cationic lipids of the present invention may have asymmetric centers, chiral axes, and chiral planes (as described in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the cationic lipids disclosed herein may exist as tautomers and both tautomeric forms are intended to be encompassed by the scope of the invention, even though only one tautomeric structure is depicted.

It is understood that substituents and substitution patterns on the cationic lipids of the instant invention can be selected by one of ordinary skill in the art to provide cationic lipids that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

It is understood that one or more Si atoms can be incorporated into the cationic lipids of the instant invention by one of ordinary skill in the art to provide cationic lipids that are chemically stable and that can be readily synthesized by techniques known in the art from readily available starting materials.

In the compounds of Formula A, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula A. For example, different isotopic forms of hydrogen (H) include protium (1H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula A can be prepared without undue experimentation by conventional techniques well known to those skilled in the art or by processes analogous to those described in the Scheme and Examples herein using appropriate isotopically-enriched reagents and/or intermediates.

As used herein, "alkyl" means a straight chain, cyclic or branched saturated aliphatic hydrocarbon having the specified number of carbon atoms.

As used herein, "alkenyl" means a straight chain, cyclic or branched unsaturated aliphatic hydrocarbon having the specified number of carbon atoms including but not limited to diene, triene and tetraene unsaturated aliphatic hydrocarbons.

Examples of a cyclic "alkyl" or "alkenyl" include:

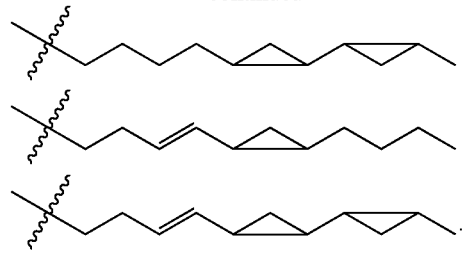

As used herein, "heterocyclyl" or "heterocycle" means a 4- to 10-membered aromatic or nonaromatic heterocycle containing from 1 to 4 heteroatoms selected from the group consisting of O, N and S, and includes bicyclic groups. "Heterocyclyl" therefore includes, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof all of which are optionally substituted with one to three substituents selected from R".

As used herein, "polyamine" means compounds having two or more amino groups. Examples include putrescine, cadaverine, spermidine, and spermine.

As used herein, "halogen" means F, Cl, Br or I.

In an embodiment of Formula A, $R^1$ and $R^2$ are each independently selected from H and $(C_1-C_6)$alkyl, wherein said alkyl is optionally substituted with one to three R'; or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three R'.

In an embodiment of Formula A, $R^1$ and $R^2$ are each independently selected from H, methyl, ethyl and propyl, wherein said methyl, ethyl and propyl are optionally substituted with one to three R'; or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three substituents selected from R'.

In an embodiment of Formula A, $R^1$ and $R^2$ are each independently selected from H, methyl, ethyl and propyl.

In an embodiment of Formula A, $R^1$ and $R^2$ are each methyl.

In an embodiment of Formula A, $R^3$ is selected from $(C_4$-$C_{20})$alkyl and $(C_4$-$C_{20})$alkenyl.

In an embodiment of Formula A, $R^3$ is $(C_{14}$-$C_{18})$alkenyl.
In an embodiment of Formula A, $R^3$ is $C_{16}$alkenyl.
In an embodiment of Formula A, $R^3$ is $C_{14}$ alkenyl.
In an embodiment of Formula A, $R^3$ is $(C_6$-$C_9)$alkyl.
In an embodiment of Formula A, $R^3$ is $C_7$alkyl.
In an embodiment of Formula A, $R^4$ is $(C_1$-$C_{16})$alkyl or $(C_2$-$C_{16})$alkenyl.
In an embodiment of Formula A, $R^4$ is $(C_4$-$C_{10})$alkenyl.
In an embodiment of Formula A, $R^4$ is $C_9$alkenyl.
In an embodiment of Formula A, $R^4$ is $(C_1$-$C_4)$alkyl.
In an embodiment of Formula A, $R^4$ is $(C_1$-$C_2)$alkyl.
In an embodiment of Formula A, $R^4$ is ethyl.
In an embodiment of Formula A, $R^4$ is methyl.
In an embodiment of Formula A, $R^3$ is $C_7$alkyl and $R^4$ is $C_9$alkenyl.
In an embodiment of Formula A, $R^3$ is $C_{14}$alkenyl and $R^4$ is ethyl.
In an embodiment of Formula A, $R^3$ is $C_{16}$alkenyl and $R^4$ is methyl.
In an embodiment of Formula A, $R^5$ is $(C_4$-$C_8)$alkyl or $(C_4$-$C_8)$alkenyl.
In an embodiment of Formula A, $R^5$ is $(C_4$-$C_8)$alkyl.
In an embodiment of Formula A, $R^5$ is $(C_6$-$C_8)$alkyl.
In an embodiment of Formula A, $R^5$ is $C_8$alkyl.
In an embodiment of Formula A, $R^6$ is methyl or ethyl.
In an embodiment of Formula A, $R^6$ is ethyl.
In an embodiment of Formula A, $R^6$ is methyl.
In an embodiment of Formula A, $R^5$ is $C_8$alkyl and $R^4$ is ethyl.
In an embodiment of Formula A, $R^5$ is $C_8$alkyl and $R^4$ is methyl.
In an embodiment of Formula A, $R^5$ is $C_7$alkyl and $R^4$ is ethyl.
In an embodiment of Formula A, $R^5$ is $C_7$alkyl and $R^4$ is methyl.
In an embodiment of Formula A, $Q^1$ and $Q^2$ are each, independently selected from a bond, —OC(O)—, —C(O)O—, —SC(O)—, —C(O)S—, —OC(S)—, —S—S—, —C(R")=N—, —N=C(R")—, —C(R")=N—O—, —O—N=C(R")—, —C(O)(NR")—, —N(R")C(O)—, C(S)(NR")—, —N(R")C(O)—, —N(R")C(O)N(R")—, —OC(O)O—, OSi(R")$_2$O—, —C(O)(CR"$_2$)C(O)O— and —OC(O)(CR"$_2$)C(O)—, with the proviso that when either $Q^1$ or $Q^2$ is a bond then the other is not a bond.

In an embodiment of Formula A, $Q^1$ and $Q^2$ are each, independently a bond or —C(O)O—, with the proviso that when either $Q^1$ or $Q^2$ is a bond then the other is not a bond.

In an embodiment of Formula A, X is selected from —OC(O)—, —C(O)O—, —SC(O)—, —C(O)S—, —OC(S)—, —S—S—, —C(R")=N—, —N=C(R")—, —C(R")=N—O—, —O—N=C(R")—, —C(O)(NR")—, —N(R")C(O)—, C(S)(NR")—, —N(R")C(O)—, —N(R")C(O)N(R")—, —OC(O)O—, OSi(R")$_2$O—, —C(O)(CR"$_2$)C(O)O— and —OC(O)(CR"$_2$)C(O)—.

In an embodiment of Formula A, X is —C(O)O—
In an embodiment of Formula A, R' is R".
In an embodiment of Formula A, R" is independently selected from H, methyl, ethyl and propyl, wherein said methyl, ethyl and propyl are optionally substituted with one or more halogen and OH.

In an embodiment of Formula A, R" is independently selected from H, methyl, ethyl and propyl.

In an embodiment of Formula A, n is 1, 2, 3, 4 or 5.
In an embodiment of Formula A, n is 3.

In an embodiment of Formula A, "heterocyclyl" is pyrolidine, piperidine, morpholine, imidazole or piperazine.

In an embodiment of Formula A, "monocyclic heterocyclyl" is pyrolidine, piperidine, morpholine, imidazole or piperazine.

In an embodiment of Formula A, "polyamine" is putrescine, cadaverine, spermidine or spermine.

In an embodiment, "alkyl" is a straight chain saturated aliphatic hydrocarbon having the specified number of carbon atoms.

In an embodiment, "alkenyl" is a straight chain unsaturated aliphatic hydrocarbon having the specified number of carbon atoms.

Included in the instant invention is the free form of cationic lipids of Formula A, as well as the pharmaceutically acceptable salts and stereoisomers thereof. Some of the isolated specific cationic lipids exemplified herein are the protonated salts of amine cationic lipids. The term "free form" refers to the amine cationic lipids in non-salt form. The encompassed pharmaceutically acceptable salts not only include the isolated salts exemplified for the specific cationic lipids described herein, but also all the typical pharmaceutically acceptable salts of the free form of cationic lipids of Formula A. The free form of the specific salt cationic lipids described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant cationic lipids can be synthesized from the cationic lipids of this invention which contain a basic or acidic moiety by conventional chemical methods. Generally, the salts of the basic cationic lipids are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the cationic lipids of this invention include the conventional non-toxic salts of the cationic lipids of this invention as formed by reacting a basic instant cationic lipids with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the cationic lipids of the present invention are acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, thiobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the cationic lipids of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

EXAMPLES

Examples provided are intended to assist in a further understanding of the invention. Particular materials employed, species and conditions are intended to be further illustrative of the invention and not limitative of the reasonable scope thereof. The reagents utilized in synthesizing the cationic lipids are either commercially available or readily prepared by one of ordinary skill in the art.

Synthesis of the novel cationic lipids is a linear process starting from lipid aldehyde (i). Addition of a lipid based Grignard reagent can generate secondary alcohol (ii). This alcohol is protected as its silyl ether (iii) and the olefin is dihydroxylated with osmium tetroxide to give diol (iv). The diol is oxidatively cleaved with sodium periodate to provide aldehyde (v). The aldehyde is converted to the carboxylic acid containing olefin (vi) by a Wittig olenfination. The acid is converted to the ester (vii) in situ, followed by silyl ether deprotection to give alcohol (viii). The alcohol is then coupled to give final compounds ix. Cyclopropanation then provides additional lipids x.

GENERAL SCHEME 1

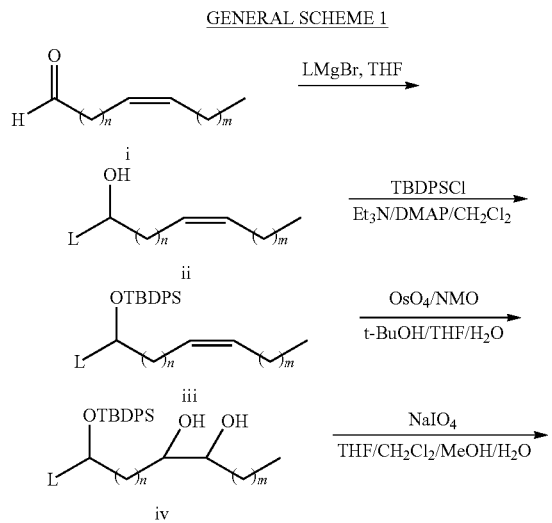

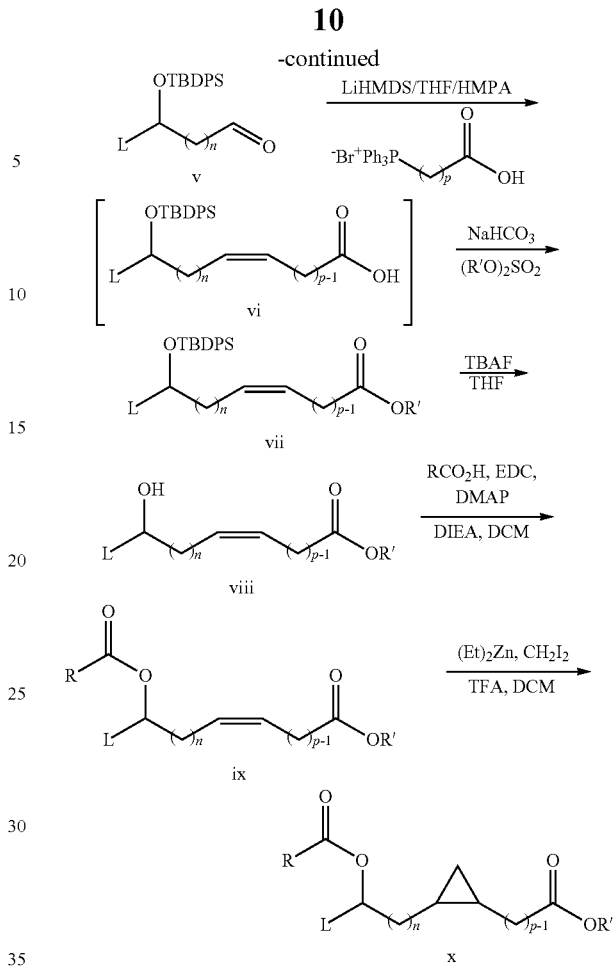

Synthesis of ester containing lipids (xiii) is achieved by oxidation of aldehyde v to carboxylic acid xi, followed by ester formation. Conversion to xiii is completed in a manner analogous to that described in General Scheme 1.

GENERAL SCHEME 2

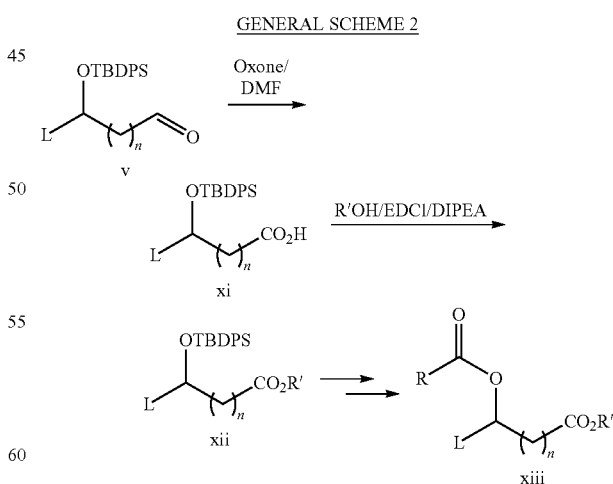

Synthesis of ester containing lipids xxi is a linear sequence beginning with carboxylic acid xiv. The acid is converted to the Weinreb amide xv followed by Grignard addition to give ketone xvi. The alcohol is deprotected, oxidized and esterified to give ester xix. Ketone xix is converted to final compound xxi via reduction and ester coupling.

GENERAL SCHEME 3

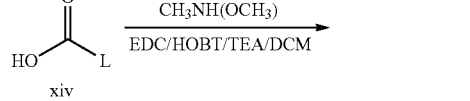

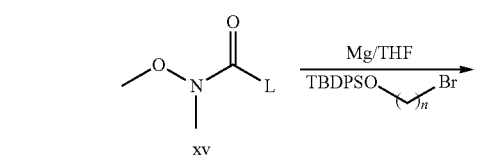

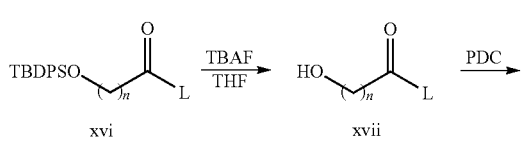

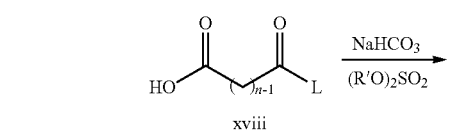

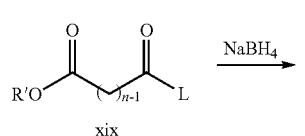

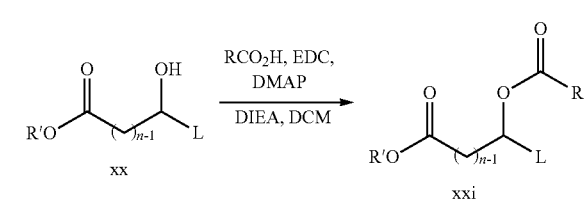

Synthesis of diester amines is accomplished as outlined in General Scheme 4. Alkene xxii is dihydroxylated and oxidatively cleaved to give aldehyde xxiv. The aldehyde is converted to the carboxylic acid containing alkene via a Wittig olefination. The resulting acid xxv is converted to its corresponding ester in situ. The silyl ether is deprotected and the alcohol oxidized to give carboxylic acid xxvii. This is esterified to give ketone intermediate xxviii. This ketone is carried on to final compound xxix as outlined in General Schemes 1 and 3 above.

GENERAL SCHEME 4

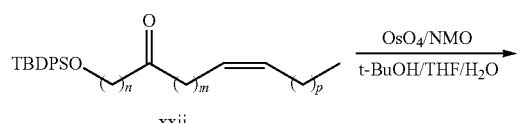

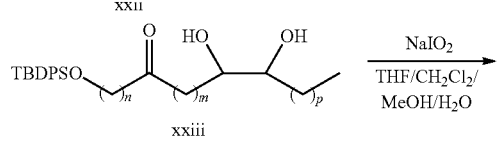

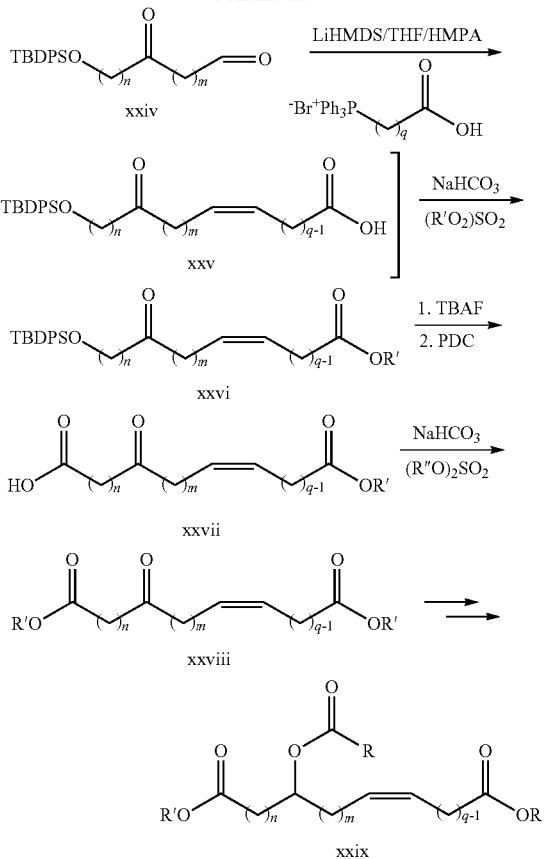

Synthesis of bis-ester compounds (xxxii) is achieved by oxidation of aldehyde (xxiv) followed by esterification to give ester xxxi. Conversion to the final compounds is achieved in a manner analogous to that described above in General Schemes 1-4.

GENERAL SCHEME 5

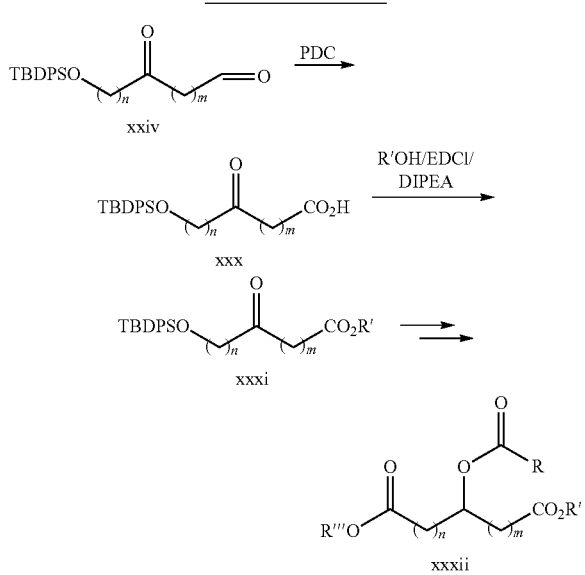

Methyl (9Z)-19-{[4-(dimethylamino)butanoyl]oxy}octacos-9-enoate (Compound 1)

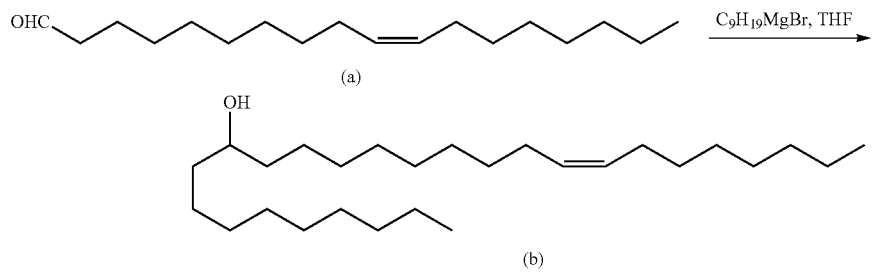

Oleyl aldehyde (a) in THF is cooled to 0° C. and treated with nonylmagnesium bromide. The reaction is warmed to room temperature and quenched with aqueous bicarbonate solution upon completion. The reaction mixture is partitioned between water and hexanes, the organics dried over sodium sulfate, filtered and evaporated in vacuo to give crude alcohol (b). The crude product is purified by flash column chromatography.

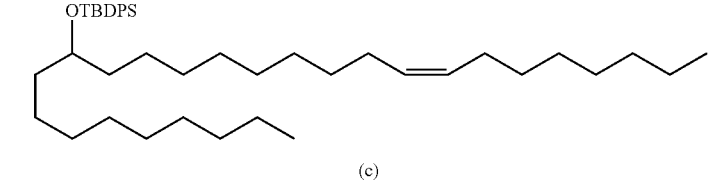

Alcohol (b) is taken up in dichloromethane and treated with triethyl amine and DMAP. To this solution is added TBDPSCl in a single portion at ambient temperature. The reaction is quenched with aqueous bicarbonate solution upon completion. The reaction mixture is partitioned between water and hexanes, the organics dried over sodium sulfate, filtered and evaporated in vacuo to give crude silyl ether (c). The crude product is purified by flash column chromatography.

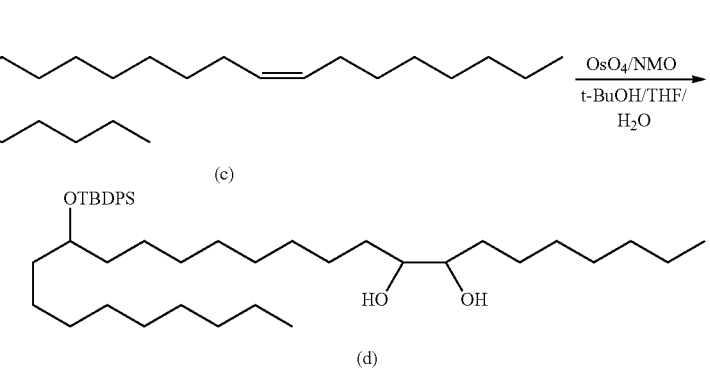

Silyl ether (c) is taken up in a mixture of tert-butanol, THF and water and treated with osmium tetroxide and NMO. The reaction is quenched with aqueous bicarbonate solution upon completion. The reaction mixture is partitioned between water and hexanes, the organics dried over sodium sulfate, filtered and evaporated in vacuo to give crude diol (d). The crude product is purified by flash column chromatography.

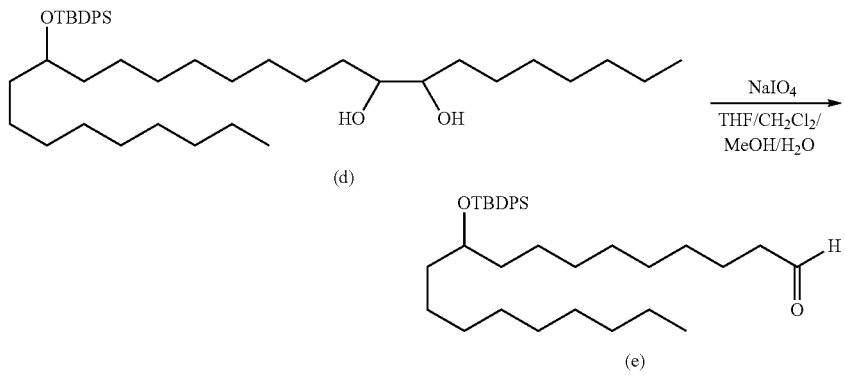

Diol (d) is taken up in a mixture of THF, dichloromethane, methanol and water and treated with sodium periodate. The reaction is quenched with aqueous bicarbonate solution upon completion. The reaction mixture is partitioned between water and hexanes, the organics dried over sodium sulfate, filtered and evaporated in vacuo to give crude aldehyde (e). The crude product is purified by flash column chromatography.

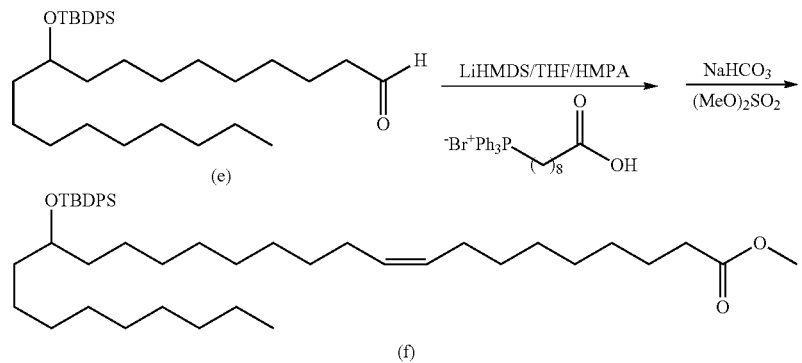

Ylide precursor triphenylphosphinium bromide is taken up in THF and treated with HMPA and lithium hexamethyldisilazide to generate the ylide. To this solution is added aldehyde (e). Upon reaction completion, the solution is treated with sodium bicarbonate and dimethylsulfate. The reaction is quenched with aqueous bicarbonate solution upon completion. The reaction mixture is partitioned between water and hexanes, the organics dried over sodium sulfate, filtered and evaporated in vacuo to give crude ester (f). The crude product is purified by flash column chromatography.

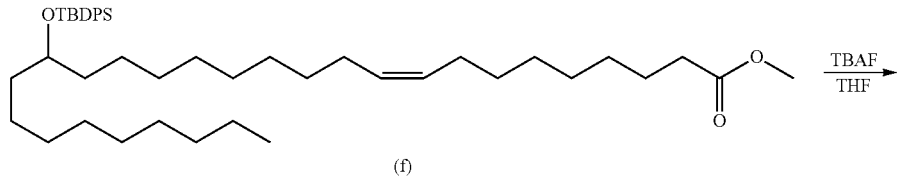

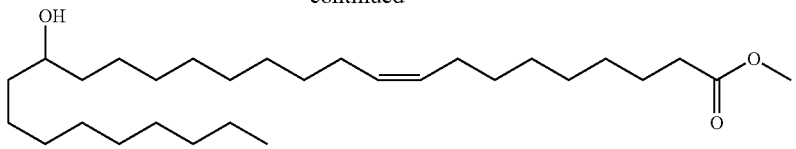

(g)

Ester (f) is taken up in THF and treated with TBAF. The reaction is quenched with aqueous bicarbonate solution upon completion. The reaction mixture is partitioned between water and hexanes, the organics dried over sodium sulfate, filtered and evaporated in vacuo to give crude alcohol (g). The crude product is purified by flash column chromatography.

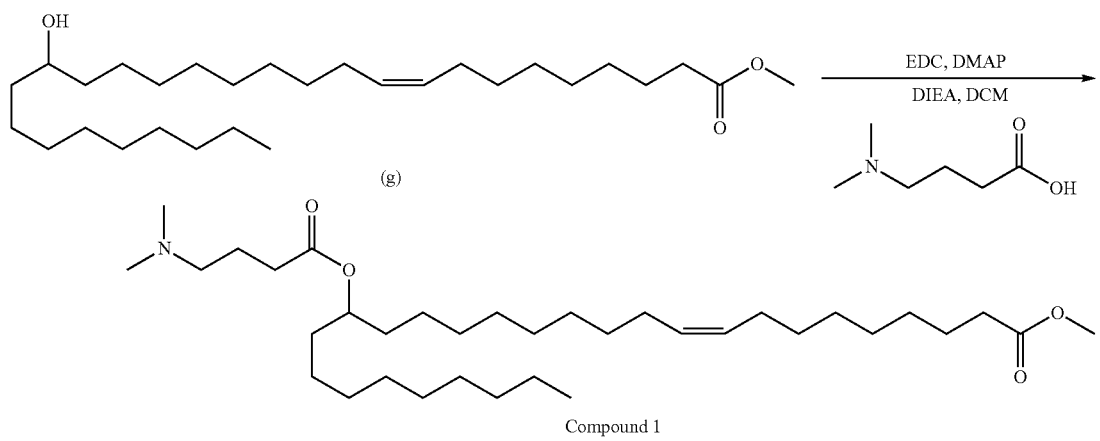

Alcohol (g) and 4-(dimethylamino)butanoic acid are taken up in dichloromethane and treated with EDC, DMAP and DIEA at ambient temperature. The reaction is quenched with aqueous bicarbonate solution upon completion. The reaction mixture is partitioned between water and hexanes, the organics dried over sodium sulfate, filtered and evaporated in vacuo to give crude Compound 1. The crude product is purified by flash column chromatography.

Methyl 8-[2-(9-{[4-(dimethylamino)butanoyl]oxy}octadecyl)cyclopropyl]octanoate (Compound 2)

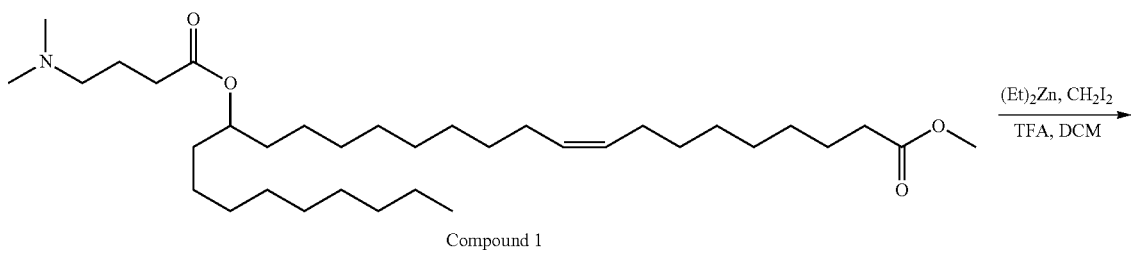

Compound 1

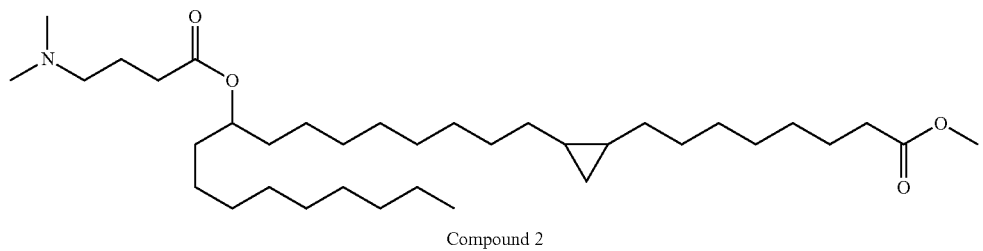

Compound 2

A solution of diethylzinc in dichloromethane is cooled to −1° C. and treated dropwise with TFA. After 30 minutes, diiodomethane is added and the resulting solution aged for 30 minutes in an ice bath. To this solution is added olefin Compound 1 and the resulting solution is warmed slowly to ambient temperature. The reaction is quenched with aqueous bicarbonate solution upon completion. The reaction mixture is partitioned between water and hexanes, the organics dried over sodium sulfate, filtered and evaporated in vacuo to give crude cyclopropane Compound 2. The crude product is purified by flash column chromatography.

Compounds 3-22 are novel cationic lipids and are prepared according to the General Scheme 1 described above.

| Compound | Structure | Name |
|---|---|---|
| 3 | 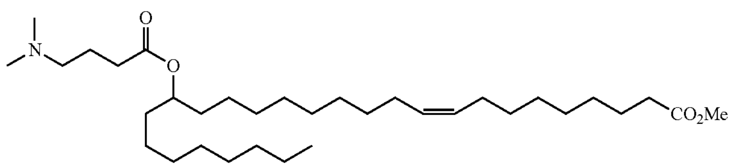 [SMILES: CCCCCCCCC(CCCCCCCC/C=C\CCCCCCCC(=O)OC)OC(=O)CCCN(C)C] | methyl (9Z)-19-{[4-(dimethylamino)butanoyl]oxy}heptacos-9-enoate |
| 4 | 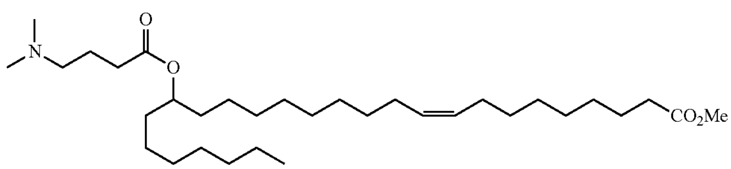 [SMILES: CCCCCCCC(CCCCCCCC/C=C\CCCCCCCC(=O)OC)OC(=O)CCCN(C)C] | methyl (9Z)-19-{[4-(dimethylamino)butanoyl oxy}hexacos-9-enoate |
| 5 | 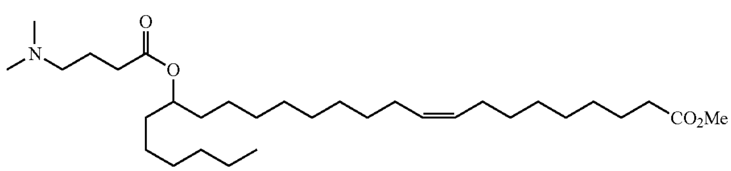 [SMILES: CCCCCCC(CCCCCCCC/C=C\CCCCCCCC(=O)OC)OC(=O)CCCN(C)C] | methyl (9Z)-19-{[4-(dimethylamino)butanoyl]oxy}pentacos-9-enoate |
| 6 | 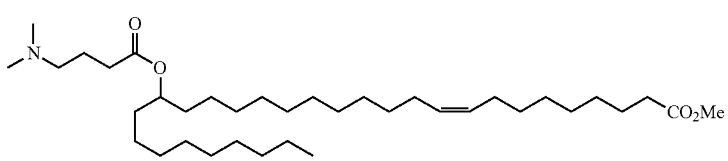 [SMILES: CCCCCCCCCC(CCCCCCCCCC/C=C\CCCCCCCC(=O)OC)OC(=O)CCCN(C)C] | methyl (9Z)-21-{[4-(dimethylamino)butanoyl]oxy}triacont-9-enoate |
| 7 | 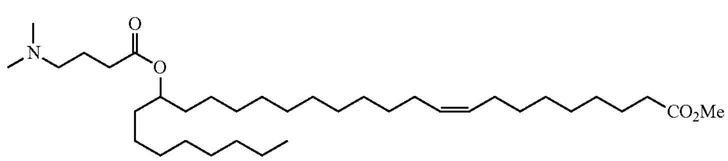 [SMILES: CCCCCCCCC(CCCCCCCCCC/C=C\CCCCCCCC(=O)OC)OC(=O)CCCN(C)C] | methyl (9Z)-21-{[4-(dimethylamino)butanoyl]oxy}nonacos-9-enoate |
| 8 | 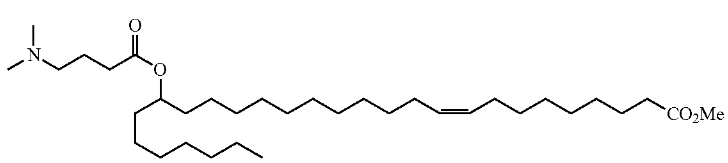 [SMILES: CCCCCCCC(CCCCCCCCCC/C=C\CCCCCCCC(=O)OC)OC(=O)CCCN(C)C] | methyl (9Z)-21-{[4-(dimethylamino)butanoyl]oxy}octacos-9-enoate |
| 9 | 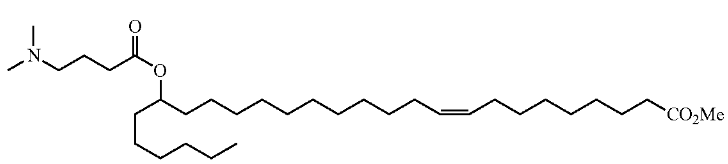 [SMILES: CCCCCCC(CCCCCCCCCC/C=C\CCCCCCCC(=O)OC)OC(=O)CCCN(C)C] | methyl (9Z)-21-{[4-(dimethylamino)butanoyl]oxy}heptacos-9-enoate |
| 10 | 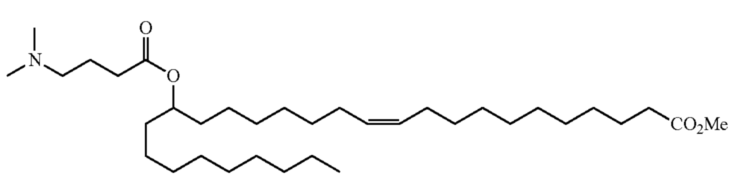 [SMILES: CCCCCCCCCC(CCCCCC/C=C\CCCCCCCCCC(=O)OC)OC(=O)CCCN(C)C] | methyl (11Z)-19-{[4-(dimethylamino)butanoyl]oxy}octacos-11-enoate |

| Compound | Structure | Name |
|---|---|---|
| 11 | 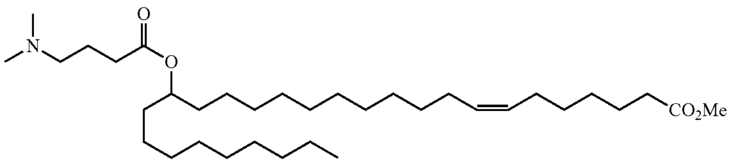 [SMILES: CCCCCCCCCC(CCCCCCCCCC/C=C\CCCCCC(=O)OC)OC(=O)CCCN(C)C] | methyl (7Z)-19-{[4-(dimethylamino)butanoyl]oxy}octacos-7-enoate |
| 12 | 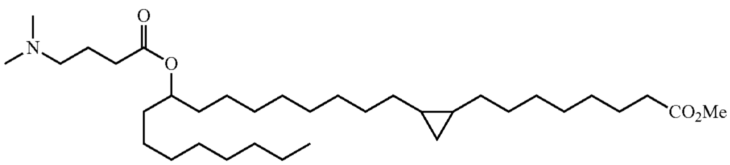 [SMILES: CCCCCCCCC(CCCCCCCCC1CC1CCCCCCCC(=O)OC)OC(=O)CCCN(C)C] | methyl 8-[2-(9-{[4-(dimethylamino)butanoyl]oxy}heptadecyl)cyclopropyl]octanoate |
| 13 | 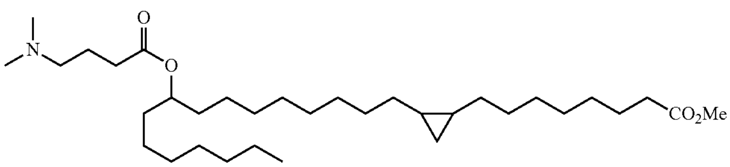 [SMILES: CCCCCCCC(CCCCCCCCC1CC1CCCCCCCC(=O)OC)OC(=O)CCCN(C)C] | methyl 8-[2-(9-{[4-(dimethylamino)butanoyl]oxy}hexadecyl)cyclopropyl]octanoate |
| 14 | 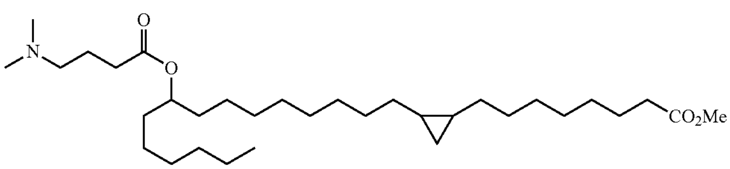 [SMILES: CCCCCCC(CCCCCCCCC1CC1CCCCCCCC(=O)OC)OC(=O)CCCN(C)C] | methyl 8-[2-(9-{[4-(dimethylamino)butanoyl]oxy}pentadecyl)cyclopropyl]octanoate |
| 15 | 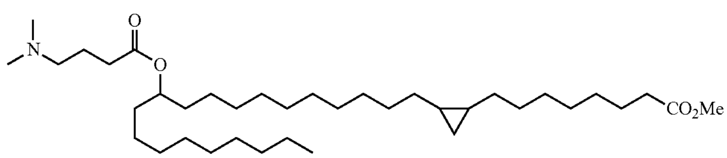 [SMILES: CCCCCCCCCC(CCCCCCCCCCC1CC1CCCCCCCC(=O)OC)OC(=O)CCCN(C)C] | methyl 8-[2-11-{[4-(dimethylamino)butanoyl]oxy}icosyl)cyclopropyl]octanoate |
| 16 | 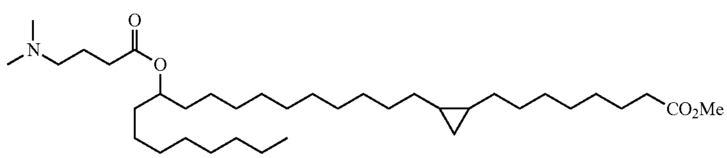 [SMILES: CCCCCCCCC(CCCCCCCCCCC1CC1CCCCCCCC(=O)OC)OC(=O)CCCN(C)C] | methyl 8-[2-(11-{[4-(dimethylamino)butanoyl]oxy}nonadecyl)cyclopropyl]octanoate |
| 17 | 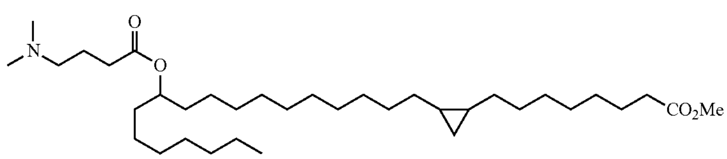 [SMILES: CCCCCCCC(CCCCCCCCCCC1CC1CCCCCCCC(=O)OC)OC(=O)CCCN(C)C] | methyl 8-{2-[11-(dimethylamino)octadecyl]cyclopropyl}octanoate |
| 18 | 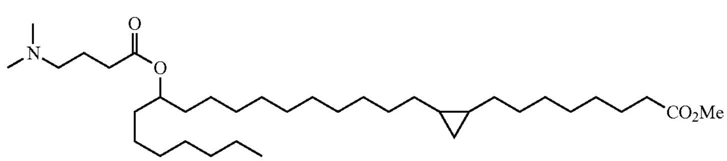 [SMILES: CCCCCCCC(CCCCCCCCCCC1CC1CCCCCCCC(=O)OC)OC(=O)CCCN(C)C] | methyl 8-[2-(11-{[4-(dimethylamino)butanoyl]oxy}octadecyl)cyclopropyl]octanoate |
| 19 | 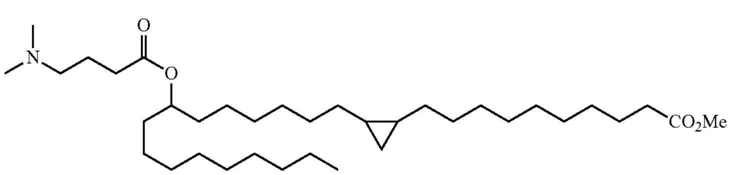 [SMILES: CCCCCCCCCC(CCCCCCC1CC1CCCCCCCCCC(=O)OC)OC(=O)CCCN(C)C] | methyl 10-[2-(7-{[4-(dimethylamino)butanoyl]oxy}hexadecyl)cyclopropyl]decanoate |

23

-continued

| Compound | Structure | Name |
|---|---|---|
| 20 | 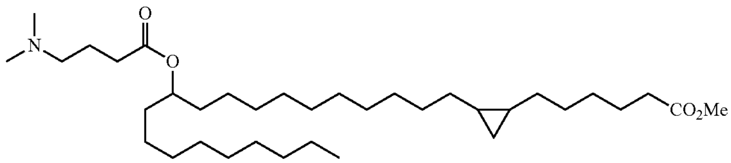 [SMILES: CCCCCCCCCC(CCCCCCCCCCC1CC1CCCCCC(=O)OC)OC(=O)CCCN(C)C] | methyl 6-[2-(11-{[4-(dimethylamino)butanoyl]oxy}icosyl)cyclopropyl]hexanoate |
| 21 | 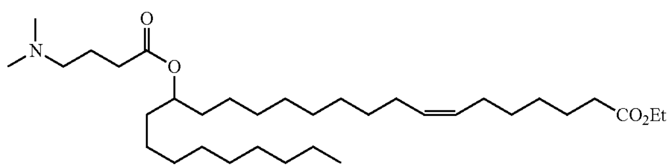 [SMILES: CCCCCCCCCC(CCCCCCCC/C=C\CCCCCC(=O)OCC)OC(=O)CCCN(C)C] | ethyl (7Z)-17-{[4-(dimethylamino)butanoyl]oxy}hexacos-7-enoate |
| 22 | 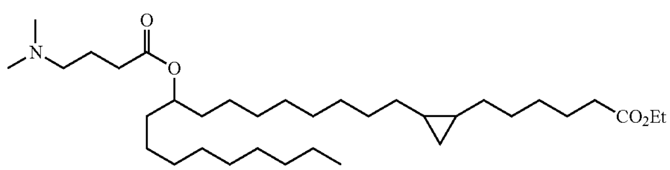 [SMILES: CCCCCCCCCC(CCCCCCCCC1CC1CCCCCC(=O)OCC)OC(=O)CCCN(C)C] | ethyl 6-[2-(9-{[4-(dimethylamino)butanoyl]oxy}octadecyl)cyclopropyl]hexanoate |

(2Z)-non-2-en-1-yl 10-{[4-(dimethylamino)butanoyl]oxy}nonadecanoate (Compound 23)

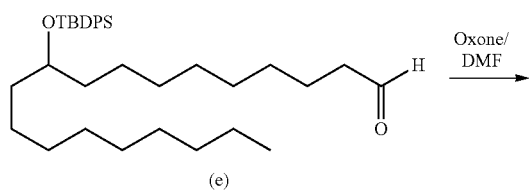

A solution of aldehyde (e) in DMF is treated with Oxone at ambient temperature. The reaction is quenched with ammonium chloride solution and partitioned between hexanes and water upon completion. The organics are dried over sodium sulfate, filtered and evaporated in vacuo to give crude acid (h). This material is purified by flash chromatography.

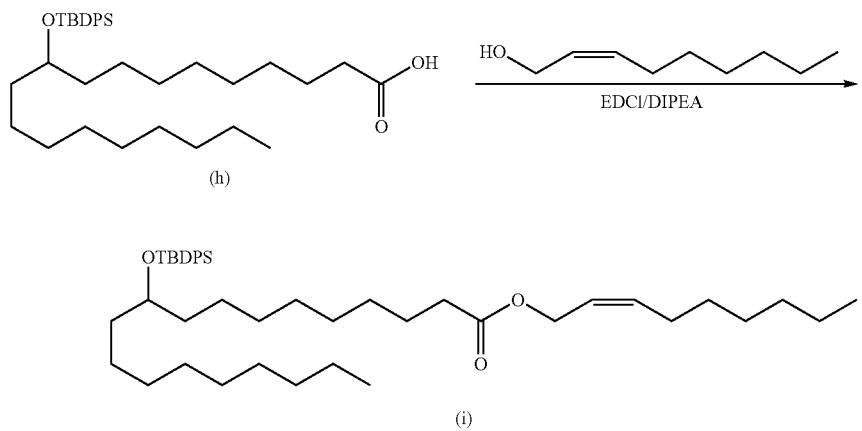

A solution of acid (h) and C9-alcohol in DMF is treated with EDCI and diisopropylethylamine. The reaction is quenched with ammonium chloride solution and partitioned between hexanes and water upon completion. The organics are dried over sodium sulfate, filtered and evaporated in vacuo to give crude acid (i). This material is purified by flash chromatography.

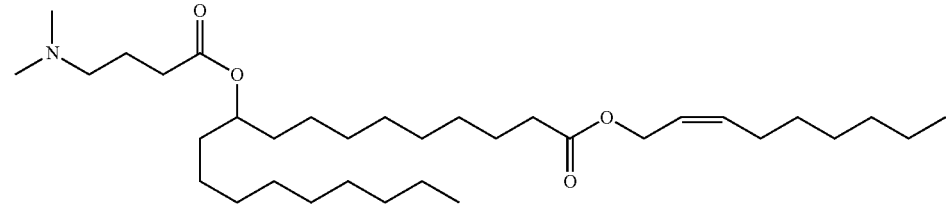

Compound 23

Conversion of silyl ether (i) to Compound 23 is carried out in a manner analogous to that described for Compound 1 above (2-hexylcyclopropyl)methyl 10-{[4-(dimethylamino)butanoyl]oxy}nonadecanoate (Compound 24)

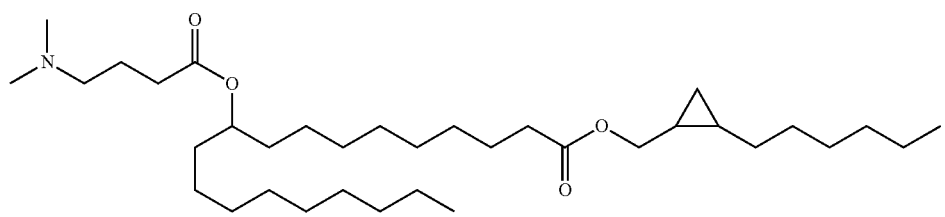

Compound 24

Compound 24 is prepared in a manner analogous to that described above for compound 23 employing the cyclopropanation chemistry as described for compound 2 above.

Compounds 25-28 are novel cationic lipids and are prepared according to General Schemes 1-2 above.

| Compound | Structure | Name |
|---|---|---|
| 25 | 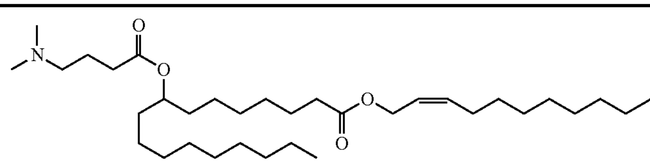 | (2Z)-undec-2-en-1-yl 8-{[4-(dimethylamino)butanoyl]oxy}heptadecanoate |
| 26 | 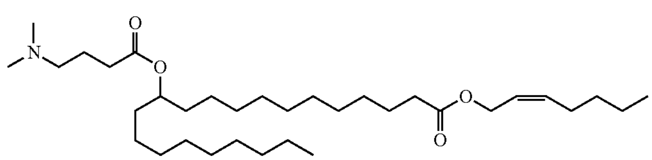 [SMILES: CCCC/C=C\COC(=O)CCCCCCCCCCC(CCCCCCCCC)OC(=O)CCCN(C)C] | (2Z)-hept-2-en-1-yl 12-{[4-(dimethylamino)butanoyl]oxy}heptadecanoate |
| 27 | 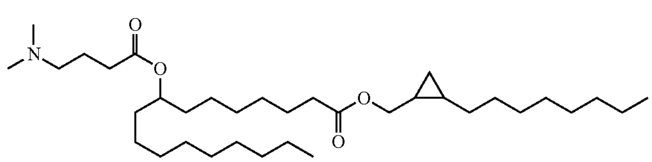 [SMILES: CCCCCCCCCC(CCCCCCC(=O)OCC1CC1CCCCCCCC)OC(=O)CCCN(C)C] | (2-octylcyclopropyl)methyl 8-{[4-(dimethylamino)butanoyl]oxy}heptadecanoate |
| 28 | 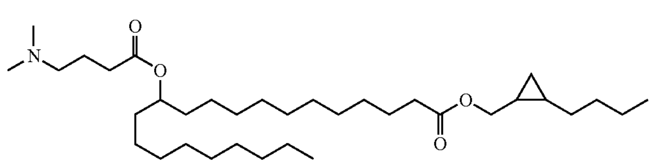 [SMILES: CCCCCCCCCC(CCCCCCCCCCC(=O)OCC1CC1CCCC)OC(=O)CCCN(C)C] | (2-butylcyclopropyl)methyl 12-{[4-(dimethylamino)butanoyl]oxy}henicosanoate |

Methyl (19Z,22Z)-9-{[4-(dimethylamino)butanoyl]oxy}octacosa-19,22-dienoate (Compound 29)

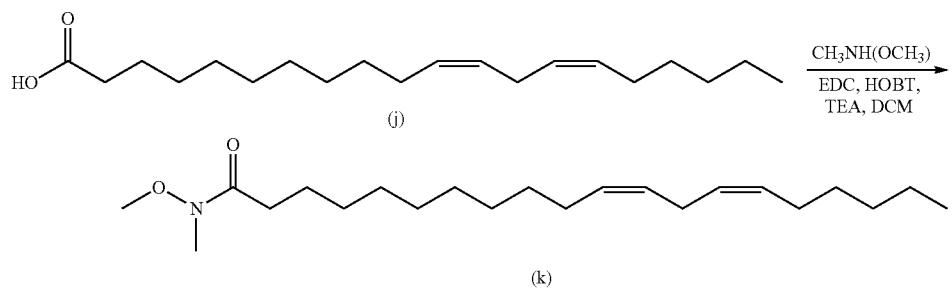

11,14-Eicosadienoic acid, (11Z,14Z)— (50 g, 162 mmol), N,O-Dimethylhydroxylamine hydrochloride (31.6 g, 324 mmol), HOAt (44.1 g, 324 mmol), Et$_3$N (45.2 mL, 324 mmol), and EDC (62.1 g, 324 mmol) were mixed in DCM (810 mL) and stirred overnight at ambient temperature. Reaction was then washed 5×700 mL water, then washed 1×600 mL 1 M NaOH, dried with sodium sulfate, filtered through celite and evaporated to obtain 53.06 g (93%) 11,14-eicosadienamide, N-methoxy-N-methyl-, (11Z,14Z) as a clear golden oil. $^1$H NMR (400 MHz, CDCl$_3$) δ 5.35 (m, 4H), 3.68 (s, 3H), 3.18 (s, 3H), 2.77 (m, 2H), 2.41 (t, J=7 Hz, 2H), 2.05 (m, 4H), 1.63 (m, 2H), 1.40-1.26 (m, 18H), 0.89 (t, J=7 Hz, 3H).

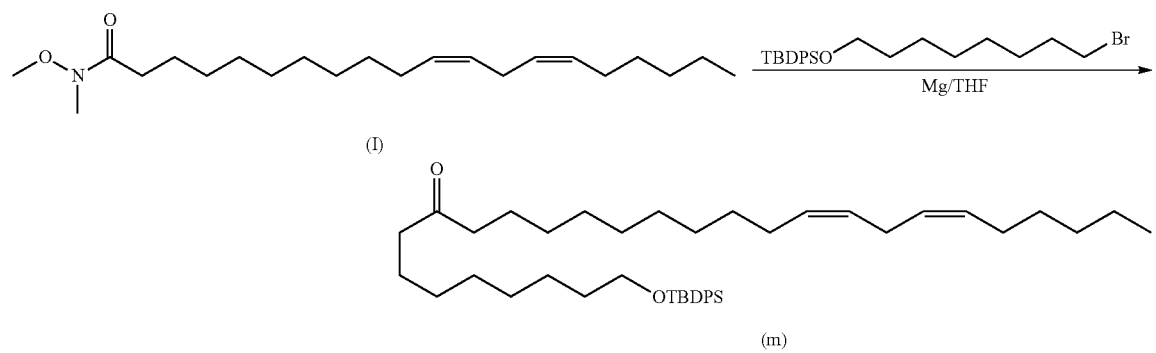

A solution of alkyl bromide in THF is treated with magnesium turnings to generate the Grignard reagent. A separate solution of Weinreb amide (1) in THF is treated with this resulting Grignard solution at ambient temperature. The reaction is quenched with ammonium chloride solution and partitioned between hexanes and water upon completion. The organics are dried over sodium sulfate, filtered and evaporated in vacuo to give crude ketone (m). This material is purified by flash chromatography.

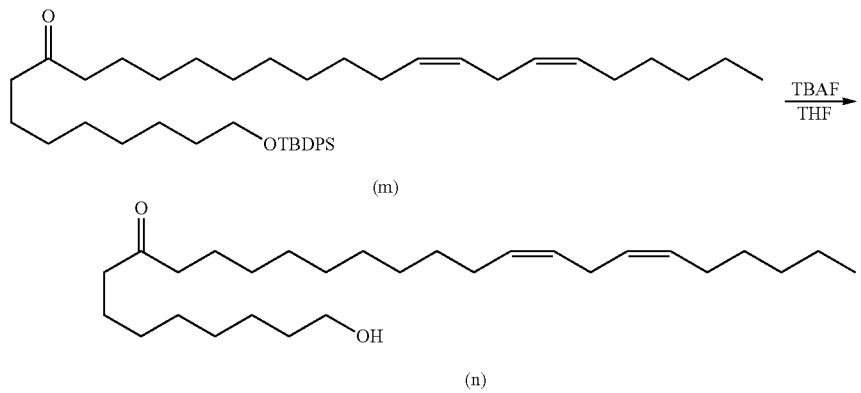

A solution of silyl ether (m) in THF is treated with TBAF. The reaction is quenched with ammonium chloride solution and partitioned between hexanes and water upon completion. The organics are dried over sodium sulfate, filtered and evaporated in vacuo to give crude alcohol (n). This material is purified by flash chromatography.

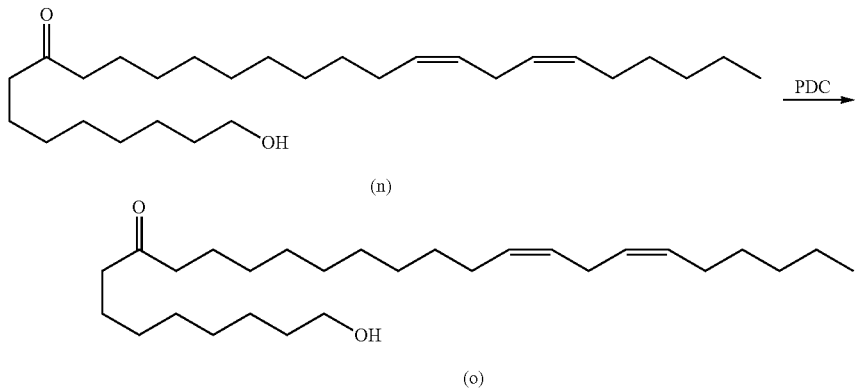

A solution of alcohol (n) in DMF is treated with pyridinium dichromate at 0° C. The solution is warmed to ambient temperature. The reaction is quenched with water and partitioned between hexanes and water upon completion. The organics are dried over sodium sulfate, filtered and evaporated in vacuo to give crude acid (o). This material is purified by flash chromatography.

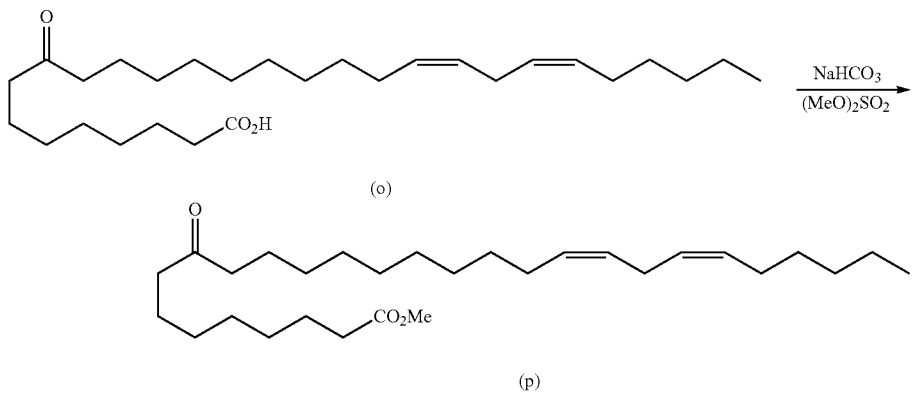

A solution of acid (o) in THF is treated with sodium bicarbonate and dimethylsulfate. The solution is warmed to ambient temperature. The reaction is quenched with sodium bicarbonate solution and partitioned between hexanes and water upon completion. The organics are dried over sodium sulfate, filtered and evaporated in vacuo to give crude keto-ester (p). This material is purified by flash chromatography.

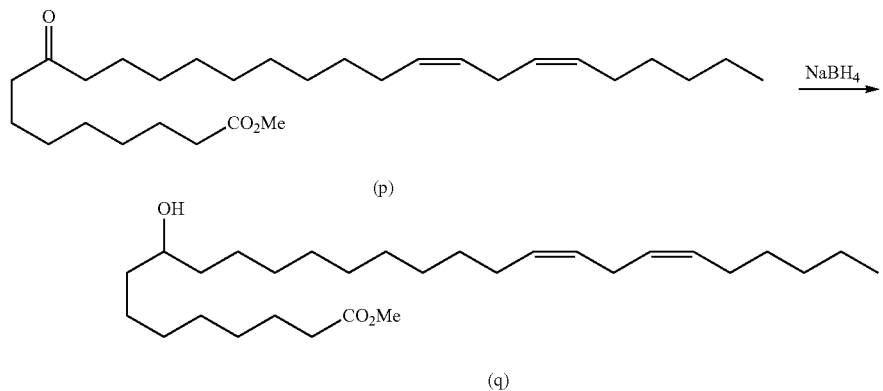

Ketone (p) is taken up in methanol and treated with sodium borohydride. The reaction is quenched with sodium bicarbonate and partitioned between water/hexanes. The organics are dried over sodium sulfate, filtered and evaporated in vacuo to give crude alcohol (q). This is purified by flash chromatography.

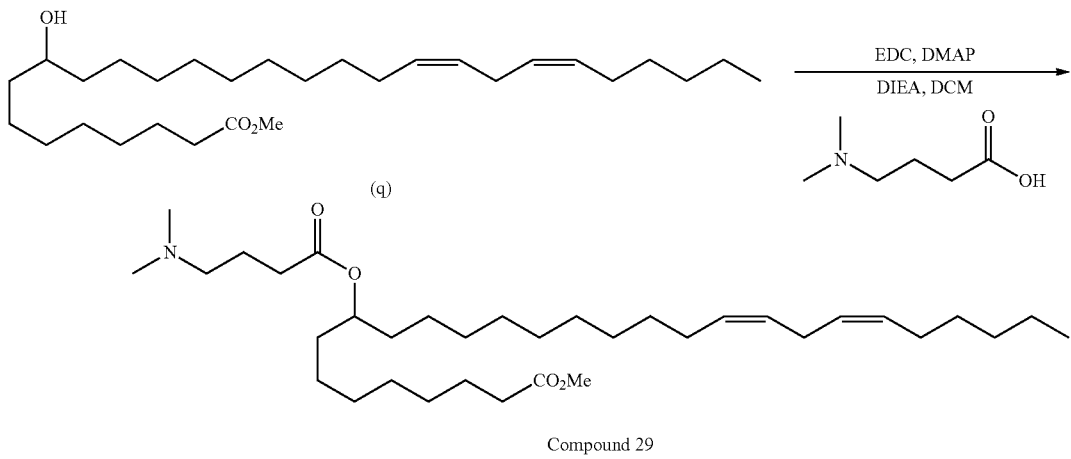

Alcohol (q) and 4-(dimethylamino)butanoic acid are taken up in dichloromethane and treated with EDC, DMAP and DIEA at ambient temperature. The reaction is quenched with aqueous bicarbonate solution upon completion. The reaction mixture is partitioned between water and hexanes, the organics dried over sodium sulfate, filtered and evaporated in vacuo to give crude lipid Compound 29. The crude product is purified by flash column chromatography.

Compounds 30-32 are novel cationic lipids and are prepared according to General Schemes 1-3 above.

| Compound | Structure | Name |
| --- | --- | --- |
| 30 | 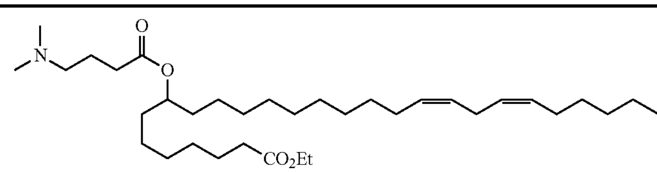 | ethyl (18Z,21Z)-8-{[4-(dimethylamino)butanoyl]oxy}heptacosa-18,21-dienoate |
| 31 | 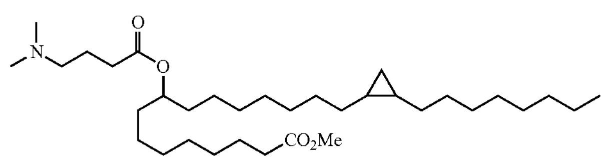 [SMILES: CCCCCCCCC1CC1CCCCCCCC(CCCCCCCC(=O)OC)OC(=O)CCCN(C)C] | methyl 9-{[4-(dimethylamino)butanoyl]oxy}-16-(2-octylcyclopropyl)hexadecanoate |
| 32 | 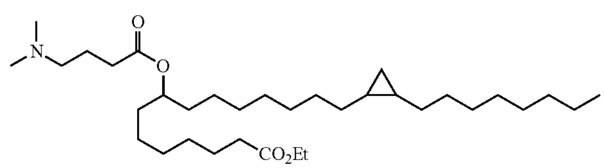 [SMILES: CCCCCCCCC1CC1CCCCCCCC(CCCCCCC(=O)OCC)OC(=O)CCCN(C)C] | ethyl 8-{[4-(dimethylamino)butanoyl]oxy}-15-(2-octycylopropyl)pentadecanoate |

Dimethyl (9Z)-19-{[4-(dimethylamino)butanoyl]oxy}heptacos-9-enedioate (Compound 33)

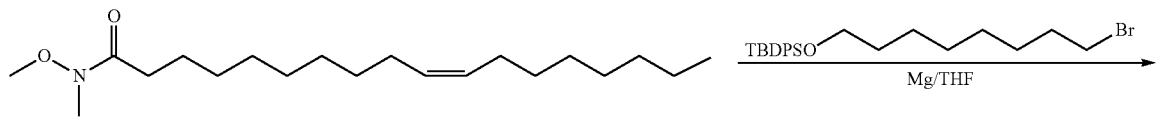

-continued

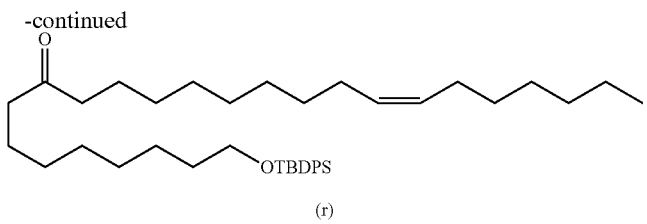

(r)

solution of alkyl bromide in THF is treated with magnesium turnings and aged to generate the Grignard reagent. A separate solution of Weinreb amide is treated with the Grignard reagent. The reaction is quenched with sodium bicarbonate solution and partitioned between hexanes and water upon completion. The organics are dried over sodium sulfate, filtered and evaporated in vacuo to give crude ketone (r). This material is purified by flash chromatography.

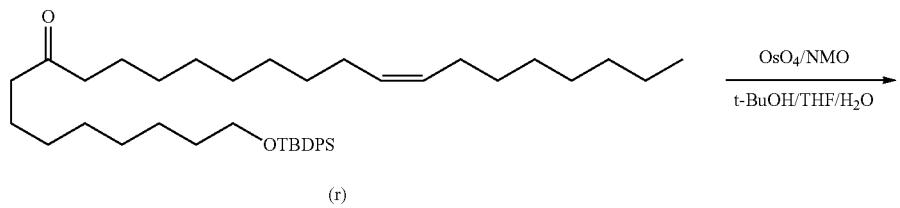

(r)

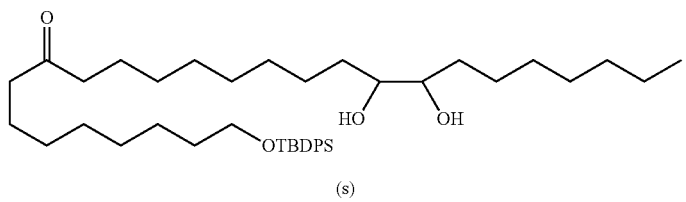

(s)

A solution of ketone in THF, tert-butanol and water is treated with osmium tetroxide and NMO. The reaction is quenched with sodium bicarbonate solution and partitioned between hexanes and water upon completion. The organics are dried over sodium sulfate, filtered and evaporated in vacuo to give crude diol (s). This material is purified by flash chromatography.

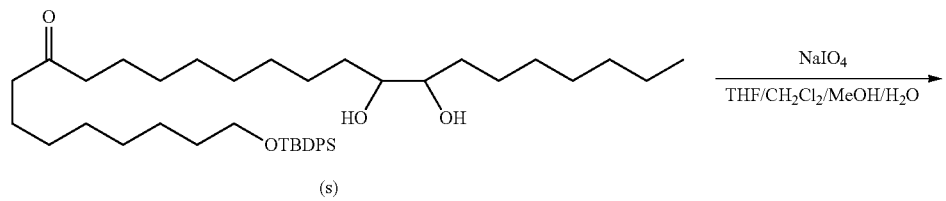

(s)

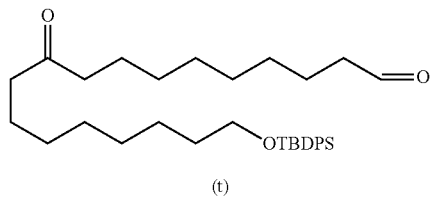

(t)

A solution of diol (s) is taken up in THF, dichloromethane, methanol and water and treated with sodium periodate. The reaction is quenched with sodium bicarbonate solution and partitioned between hexanes and water upon completion. The organics are dried over sodium sulfate, filtered and evaporated in vacuo to give crude aldehyde (t). This material is purified by flash chromatography.

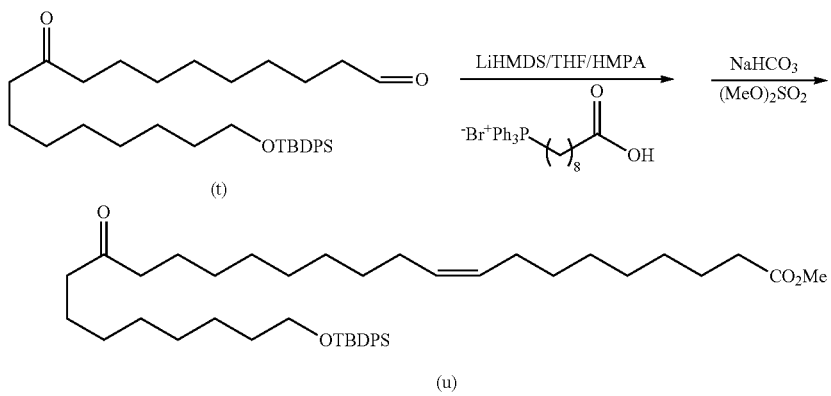

Ylide precursor triphenylphosphinium bromide is taken up in THF and treated with HMPA and lithium hexamethyldisilazide to generate the ylide. To this solution is added aldehyde (t). Upon reaction completion, the solution is treated with sodium bicarbonate and dimethylsulfate. The reaction is quenched with aqueous bicarbonate solution upon completion. The reaction mixture is partitioned between water and hexanes, the organics dried over sodium sulfate, filtered and evaporated in vacuo to give crude ester (u). The crude product is purified by flash column chromatography.

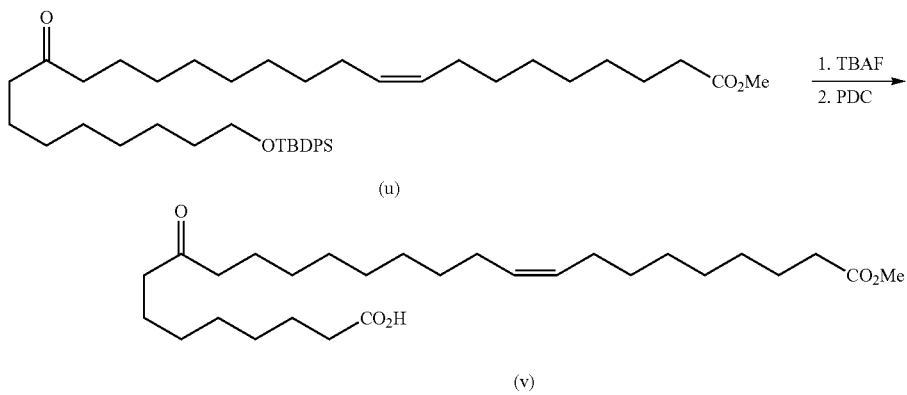

A solution of silyl ether (u) in THF is treated with TBAF. The reaction is quenched with aqueous bicarbonate solution upon completion. The reaction mixture is partitioned between water and hexanes, the organics dried over sodium sulfate, filtered and evaporated in vacuo to give crude alcohol. The crude product is purified by flash column chromatography.

A solution of alcohol in DMF is treated with pyridinium dichromate. The reaction is quenched with water upon completion. The reaction mixture is partitioned between water and hexanes, the organics dried over sodium sulfate, filtered and evaporated in vacuo to give crude acid (v). The crude product is purified by flash column chromatography.

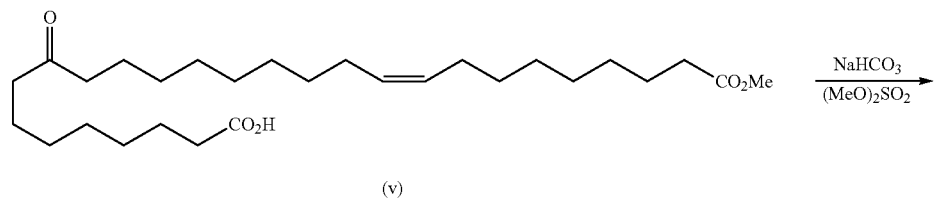

-continued

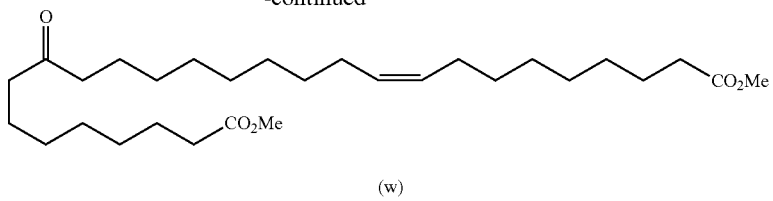

(w)

A solution of acid (v) in THF is treated with sodium bicarbonate and dimethyl sulfate. The reaction is quenched with aqueous bicarbonate solution upon completion. The reaction mixture is partitioned between water and hexanes, the organics dried over sodium sulfate, filtered and evaporated in vacuo to give crude diester (w). The crude product is purified by flash column chromatography.

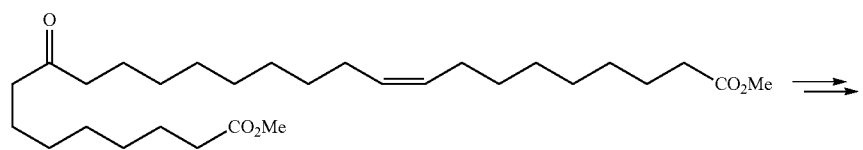

(w)

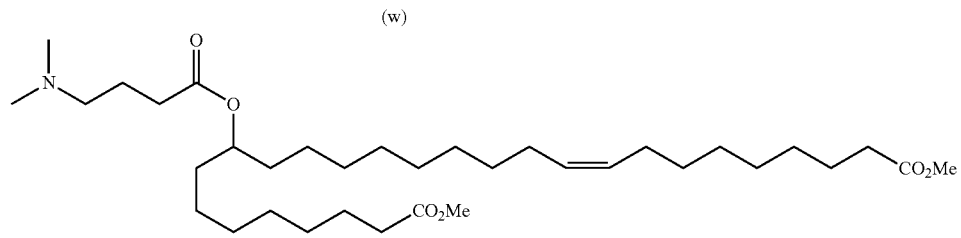

Compound 33

Ketone (w) is converted to amine Compound 33 in a manner analogous to that described for Compound 29.

Diesters similar to Compound 33 are prepared wherein modifications to the structure are similar to those outlined in the tables above, i.e. varying lipid chain lengths, methyl and ethyl esters, inclusion of cylcopropanes, modifying position of unsaturation or cyclopropane incorporation, and all possible combinations of above.

1-Methyl 18-[(2Z)-non-2-en-1-yl 9-{4-(dimethyl-amino)butanoyl]oxy}octadecanedioate (Compound 34)

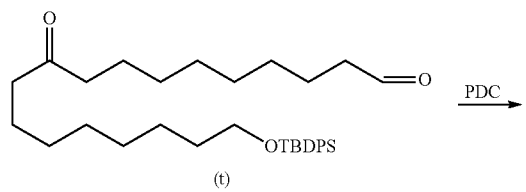

(t)

-continued

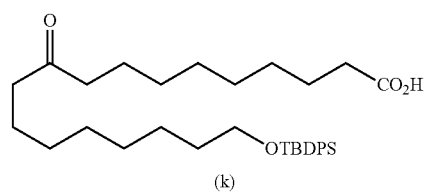

(k)

A solution of aldehyde (t) in DMF is treated with pyridinium dichromate. The reaction is quenched with aqueous bicarbonate solution upon completion. The reaction mixture is partitioned between water and hexanes, the organics dried over sodium sulfate, filtered and evaporated in vacuo to give crude acid (x). The crude product is purified by flash column chromatography.

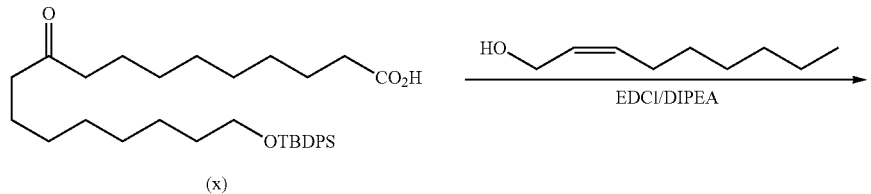

(x)

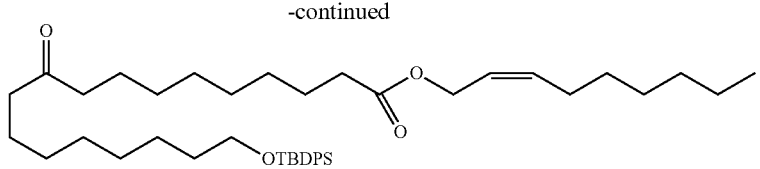

(y)

A solution of acid (x) in dichloromethane is treated with C9 alcohol and EDCI and diisopropylethylamine. The reaction is quenched with aqueous bicarbonate solution upon completion. The reaction mixture is partitioned between water and hexanes, the organics dried over sodium sulfate, filtered and evaporated in vacuo to give crude keto ester (y). The crude product is purified by flash column chromatography.

34

Ketone (y) is converted to amine Compound 34 in a manner analogous to that described for Compound 33 above.

Diesters similar to Compound 34 are prepared wherein modifications to the structure are similar to those outlined in the tables above, i.e. varying lipid chain lengths, methyl and ethyl esters, inclusion of cylcopropanes, modifying position of unsaturation or cyclopropane incorporation, and all possible combinations of above.

LNP COMPOSITIONS

The following lipid nanoparticle compositions (LNPs) of the instant invention are useful for the delivery of oligonucleotides, specifically siRNA and miRNA:
Cationic Lipid/Cholesterol/PEG-DMG 56.6/38/5.4;
Cationic Lipid/Cholesterol/PEG-DMG 60/38/2;
Cationic Lipid/Cholesterol/PEG-DMG 67.3/29/3.7;
Cationic Lipid/Cholesterol/PEG-DMG 49.3/47/3.7;
Cationic Lipid/Cholesterol/PEG-DMG 50.3/44.3/5.4;
Cationic Lipid/Cholesterol/PEG-C-DMA/DSPC 40/48/2/10;
Cationic Lipid/Cholesterol/PEG-DMG/DSPC 40/48/2/10; and
Cationic Lipid/Cholesterol/PEG-DMG/DSPC 58/30/2/10.

LNP Process Description:

The Lipid Nano-Particles (LNP) is prepared by an impinging jet process. The particles are formed by mixing lipids dissolved in alcohol with siRNA dissolved in a citrate buffer. The mixing ratio of lipids to siRNA are targeted at 45-55% lipid and 65-45% siRNA. The lipid solution can contain a novel cationic lipid of the instant invention, a helper lipid (cholesterol), PEG (e.g. PEG-C-DMA, PEG-DMG) lipid, and DSPC at a concentration of 5-15 mg/mL with a target of 9-12 mg/mL in an alcohol (for example ethanol). The ratio of the lipids can have a mole percent range of 25-98 for the cationic lipid with a target of 35-65, the helper lipid can have a mole percent range from 0-75 with a target of 30-50, the PEG lipid can have a mole percent range from 1-15 with a target of 1-6, and the DSPC can have a mole percent range of 0-15 with a target of 0-12. The siRNA solution can contain one or more siRNA sequences at a concentration range from 0.3 to 1.0 mg/mL with a target of 0.3-0.9 mg/mL in a sodium citrate buffered salt solution with pH in the range of 3.5-5. The two liquids are heated to a temperature in the range of 15-40° C., targeting 30-40° C., and then mixed in an impinging jet mixer instantly forming the LNP. The teeID can have a range from 0.25 to 1.0 mm and a total flow rate from 10-600 mL/min. The combination of flow rate and tubing ID can have the effect of controlling the particle size of the LNPs between 30 and 200 nm. The solution can then be mixed with a buffered solution at a higher pH with a mixing ratio in the range of 1:1 to 1:3 vol:vol but targeting 1:2 vol:vol. This buffered solution is at a temperature in the range of 15-40° C., targeting 30-40° C. The mixed LNPs are held from 30 minutes to 2 hrs prior to an anion exchange filtration step. The temperature during incubating is in the range of 15-40° C., targeting 30-40° C. After incubating the solution is filtered through a 0.8 um filter containing an anion exchange separation step. This process can use tubing IDs ranging from 1 mm ID to 5 mm ID and a flow rate from 10 to 2000 mL/min. The LNPs are concentrated and diafiltered via an ultrafiltration process where the alcohol is removed and the citrate buffer is exchanged for the final buffer solution such as phosphate buffered saline. The ultrafiltration process can use a tangential flow filtration format (TFF). This process can use a membrane nominal molecular weight cutoff range from 30-500 KD. The membrane format is hollow fiber or flat sheet cassette. The TFF processes with the proper molecular weight cutoff can retain the LNP in the retentate and the filtrate or permeate contains the alcohol; citrate buffer; final buffer wastes. The TFF process is a multiple step process with an initial concentration to a siRNA concentration of 1-3 mg/mL. Following concentration, the LNPs solution is diafiltered against the final buffer for 10-20 volumes to remove the alcohol and perform buffer exchange. The material can then be concentrated an additional 1-3 fold. The final steps of the LNP process are to sterile filter the concentrated LNP solution and vial the product.

Analytical Procedure:

1) siRNA Concentration

The siRNA duplex concentrations are determined by Strong Anion-Exchange High-Performance Liquid Chromatography (SAX-HPLC) using Waters 2695 Alliance system (Water Corporation, Milford Mass.) with a 2996 PDA detector. The LNPs, otherwise referred to as RNAi Delivery Vehicles (RDVs), are treated with 0.5% Triton X-100 to free total siRNA and analyzed by SAX separation using a Dionex BioLC DNAPac PA 200 (4×250 mm) column with UV detection at 254 nm. Mobile phase is composed of A: 25 mM $NaClO_4$, 10 mM Tris, 20% EtOH, pH 7.0 and B: 250 mM $NaClO_4$, 10 mM Tris, 20% EtOH, pH 7.0 with liner gradient from 0-15 min and flow rate of 1 ml/min. The siRNA amount is determined by comparing to the siRNA standard curve.

2) Encapsulation Rate

Fluorescence reagent SYBR Gold is employed for RNA quantitation to monitor the encapsulation rate of RDVs. RDVs with or without Triton X-100 are used to determine the free siRNA and total siRNA amount. The assay is performed using a SpectraMax M5e microplate spectrophotometer from Molecular Devices (Sunnyvale, Calif.). Samples are excited at 485 nm and fluorescence emission is measured at 530 nm. The siRNA amount is determined by comparing to the siRNA standard curve.

Encapsulation rate=(1−free siRNA/total siRNA)× 100%

3) Particle Size and Polydispersity

RDVs containing 1 µg siRNA are diluted to a final volume of 3 ml with 1×PBS. The particle size and polydispersity of the samples is measured by a dynamic light scattering method using ZetaPALS instrument (Brookhaven Instruments Corporation, Holtsville, N.Y.). The scattered intensity is measured with He—Ne laser at 25° C. with a scattering angle of 90°.

4) Zeta Potential Analysis

RDVs containing 1 µg siRNA are diluted to a final volume of 2 ml with 1 mM Tris buffer (pH 7.4). Electrophoretic mobility of samples is determined using ZetaPALS instrument (Brookhaven Instruments Corporation, Holtsville, N.Y.) with electrode and He—Ne laser as a light source. The Smoluchowski limit is assumed in the calculation of zeta potentials.

5) Lipid Analysis

Individual lipid concentrations is determined by Reverse Phase High-Performance Liquid Chromatography (RP-HPLC) using Waters 2695 Alliance system (Water Corporation, Milford Mass.) with a Corona charged aerosol detector (CAD) (ESA Biosciences, Inc, Chelmsford, Mass.). Individual lipids in RDVs are analyzed using an Agilent Zorbax SB-C18 (50×4.6 mm, 1.8 µm particle size) column with CAD at 60° C. The mobile phase is composed of A: 0.1% TFA in $H_2O$ and B: 0.1% TFA in IPA. The gradient can change from 60% mobile phase A and 40% mobile phase B from time 0 to 40% mobile phase A and 60% mobile phase B at 1.00 min; 40% mobile phase A and 60% mobile phase B from 1.00 to 5.00 min; 40% mobile phase A and 60% mobile phase B from 5.00 min to 25% mobile phase A and 75% mobile phase B at 10.00 min; 25% mobile phase A and 75% mobile phase B from 10.00 min to 5% mobile phase A and 95% mobile phase B at 15.00 min; and 5% mobile phase A and 95% mobile phase B from 15.00 to 60% mobile phase A and 40% mobile phase B at 20.00 min with flow rate of 1 ml/min. The individual lipid concentration is determined by comparing to the standard curve with all the lipid components in the RDVs with a quadratic curve fit. The molar percentage of each lipid is calculated based on its molecular weight.

Utilizing the above described LNP process, specific LNPs with the following ratios are identified:

Nominal Composition:
Cationic Lipid/Cholesterol/PEG-DMG 60/38/2
Cationic Lipid/Cholesterol/PEG-DMG/DSPC 58/30/2/10
Luc siRNA

```
                                          (SEQ. ID. NO.: 1)
5'-iB-AUAAGGCUAUGAAGAGAUAUU-iB 3'

(SEQ. ID. NO.: 2)
3'-UUUAUUCCGAUACUUCUCUAU-5'
AUGC-Ribose
iB-Inverted deoxy abasic
UC-2' Flouro
AGT-2' Deoxy
AGU-2' OCH3
```

Nominal Composition
Cationic Lipid/Cholesterol/PEG-DMG 60/38/2
Cationic Lipid/Cholesterol/PEG-DMG/DSPC 40/48/2/10
Cationic Lipid/Cholesterol/PEG-DMG/DSPC 58/30/2/10
ApoB siRNA

```
                                          (SEQ ID NO.: 3)
5'-iB-CUUUAACAAUUCCUGAAAUTsT-iB-3'

(SEQ ID NO.: 4)
3'-UsUGAAAUUGUUAAGGACUsUsUsA-5'
AUGC-Ribose
iB-Inverted deoxy abasic
UC-2' Flouro
AGT-2' Deoxy
AGU-2' OCH3
UsA-phortherothioate linkage beta-catenin siRNA
                                          (SEQ ID NO.: 5)
5'-iB-CUGUUGGAUUGAUUCGAAAUsU-iB-3''

(SEQ ID NO.: 6)
3'-UsUGACAACCUAACUAAGCUUU-5'
AUGC-Ribose
iB-Inverted deoxy abasic
UC-2' Fluoro
AGT-2' Deoxy
AGU-2' OCH3
UsA-phophorothioate linkage (SEQ ID NO.: 7)
5'-iB-ACGACUAGUUCAGUUGCUUUsU-iB-3'

(SEQ ID NO.: 8)
3'-UsUUGCUGAUCAAGUCAACGAA-5'
AUGC-Ribose
iB-Inverted deoxy abasic
UC-2' Fluoro
AGT-2' Deoxy
AGU-2' OCH3
UsA-phophorothioate linkage (SEQ ID NO.: 9)
5'-iB-ACGACUAGUUCAGUUGCUUUU-iB-3'

(SEQ ID NO.: 10)
3'-UUUGCUGAUCAAGUCAACGAA-5'
AUGC-Ribose
iB-Inverted deoxy abasic
UC-2' Fluoro
AGT-2' Deoxy
AGU-2' OCH3
UsA-phophorothioate linkage
```

Oligonucleotide synthesis is well known in the art. (See US patent applications: US 2006/0083780, US 2006/0240554, US 2008/0020058, US 2009/0263407 and US 2009/0285881 and PCT patent applications: WO 2009/086558, WO2009/127060, WO2009/132131, WO2010/042877, WO2010/054384, WO2010/054401, WO2010/054405 and WO2010/054406). The siRNAs disclosed and utilized in the Examples are synthesized via standard solid phase procedures.

Example 1

Mouse In Vivo Evaluation of Efficacy

LNPs utilizing Compounds 1-34, in the nominal compositions described immediately above, are evaluated for in vivo efficacy. The siRNA can target the mRNA transcript for the firefly (*Photinus pyralis*) luciferase gene (Accession # M15077). The primary sequence and chemical modification pattern of the luciferase siRNA is displayed above. The in vivo luciferase model employs a transgenic mouse in which the firefly luciferase coding sequence is present in all cells. ROSA26-LoxP-Stop-LoxP-Luc (LSL-Luc) transgenic mice licensed from the Dana Farber Cancer Institute are induced to express the Luciferase gene by first removing the LSL sequence with a recombinant Ad-Cre virus (Vector Biolabs). Due to the organo-tropic nature of the virus, expression is limited to the liver when delivered via tail vein injection. Luciferase expression levels in liver are quantitated by measuring light output, using an IVIS imager (Xenogen) following administration of the luciferin substrate (Caliper Life Sciences). Pre-dose luminescence levels is measured prior to administration of the RDVs. Luciferin in PBS (15 mg/mL) is intraperitoneally (IP) injected in a volume of 150 µL. After a four minute incubation period mice are anesthetized with isoflurane and placed in the IVIS imager. The RDVs (containing siRNA) in PBS vehicle are tail vein injected in a volume of 0.2 mL. Final dose levels can range from 0.1 to 0.5 mg/kg siRNA. PBS vehicle alone is dosed as a control. Mice are imaged 48 hours post dose using the method described above. Changes in luciferin light output directly correlate with luciferase mRNA levels and represent an indirect measure of luciferase siRNA activity. In vivo efficacy results are expressed as % inhibition of luminescence relative to pre-dose luminescence levels.

Example 2

In Vitro ApoE Binding Assay

LNPs are incubated at 37° C. in 90% rhesus serum at a final LNP concentration of 4 ug/mL. Incubation is for 20 minutes with orbital rotation. After incubation, the samples are diluted 1:20 in PBS and 100 µL of each diluted sample is aliquoted to wells of an anti-PEG antibody coated 96-well plate (Life Diagnostics Cat. No. P-0001PL. After incubation at room temperature for 1 hour, the plate is washed 5× with 300 uL PBS. After washing, 50 uL of 0.2% Triton X-100 is added to each well and the plate incubated at 37° C. for 10 minutes, followed by shaking on a plate shaker for 1 minute at 750 rpm. Samples are frozen prior to performing the ApoE ELISA and stem loop PCR analysis of samples.

An ApoE ELISA assay is performed to quantitate ApoE bound to the LNPs after incubation in rhesus serum. Anti-ApoE antibody (Milipore, Cat No. AB947) is diluted 1:1000 in PBS and 100 µL of diluted antibody is added to each well of a polystyrene high binding plate. The plate with antibody is incubated overnight at 4° C., after which the plate is washed 2× with 200 µL of PBS. Next, 200 µL of buffer containing 1% BSA and 0.05% Tween-20 in PBS (Incubation Buffer) is added to each well followed by incubation at room temperature for 1 hour. Plates are washed 5× with PBS containing 0.05% Tween-20. Frozen Triton lysis test samples are thawed and diluted 1:6 with incubation buffer and 100 µL of test sample is aliquoted to wells of the ApoE antibody plate. Incubation is for 1 hour at room temperature followed by a 5× wash with PBS containing 0.05% Tween-20. After washing, 100 µL of biotinylated anti-ApoE antibody (Mabtech, Cat. ANo. E887-biotin), diluted 1:500 in incubation buffer, is added to each well and incubated for 1 hour at room temperature, followed by a 5× wash with 0.05% Tween-20 in PBS. 100 µL per well, of Streptavidin-HPR (Thermo, Cat. No. TS-125-HR), is then added and incubated for 1 hour at room temperature. After washing 5× with 0.05% Tween-20 in PBS, 100 µL of TMB Substrate (Thermo, Cat. No. 34028) is added to each well, followed by incubation at room temperature for 20 minutes in the dark. The colorimetric reaction is stopped with 100 µL of TMB Stop Solution (KPL, Cat. No. 50-85-04) and absorbance at 450 nm is determined. An ApoE standard curve is prepared by diluting rhesus Recombinant ApoE in incubation buffer with 0.03% Triton X-100 with concentrations ranging from 100 ng/mL to 0.78 ng/mL. ApoE standards are evaluated in the ELISA in parallel to the test samples. A rhesus serum only (no LNP) control is utilized to obtain a background subtraction for non-LNP dependent ApoE signal in the ELISA.

Stem Loop RT-PCR Protocol

To normalize to the ApoE bound to the amount of LNP bound to the anti-PEG antibody plate, the amount of siRNA retained in the anti-PEG antibody well is quantitated by stem-loop PCR and related to the number of siRNAs encapsulated per LNP, to give an approximate measure of total LNP particles bound per well.

Preparation of the Spiked Standard Curve Samples:

The standard curve is prepared using the molecular weight of the siRNA (13693 g/mol for ApoB 17063) to calculate the copy number. The high standard should contain $10^{11}$ copies per 3 µl. A 10-fold serial dilution is performed across a row of an assay plate until the lowest standard contains $10^2$ copies per 3.1. One could dilute 0.2% Triton X-100 1:80 in water and pipette 20 µL of the diluted Triton X-100 into 10 wells of a 96 well plate. 30 µL of the serial diluted standard curve and mix is added to each well of the plate. 10 µL of the spiked standard curve is used in the reverse transcription reaction.

Stem-Loop RT-PCR—Test Samples and Standard Curve:

Triton lysates from the PEG antibody plate capture is diluted 1 to 2000 in nuclease free water. 10 µL of 'RT-Primer Mix' (Applied Biosystem's TaqMan MicroRNA Reverse Transcription Kit Cat. No. 4366596) is added to each well of a 96-well Micro-Amp QPCR plate (ABI Cat# N801-0560).

| RT Primer Mix Components | µL/rxn | Final conc. |
|---|---|---|
| ApoB RT-primer (10 uM) | 0.6 | 200 nM |
| 10× buffer | 2 | |
| Water | 7.4 | |

ApoB RT primer sequence:
(SEQ. ID. NO.: 11)
5' GTCGTATCCAGTGCAGGGTCCGAGGTATTCGCACTGGATACGAC
CTTTAACA3'

10 μL of each test sample (diluted 1 to 2000) or spiked standard curve (above) is aliquoted into the 96-well plate. The plate is covered with a mat (ABI Cat. No. N801-0550), to minimize evaporation. The plate is briefly centrifuged at 800 rpm for 1 minute. Next, the plate is run on a thermocycler using the following cycling parameters:

| Cycling: | 94° C. | 10 minutes |
|---|---|---|
| | 75° C. | 2 minutes |
| | 60° C. | 3 minutes |
| | 50° C. | 3 minutes |
| | 40° C. | 3 minutes |
| | 30° C. | 3 minutes |
| | 4° C. | hold |

Next, 10 μL of 'RT Mix' is added to each well (Applied Biosystem's TaqMan MicroRNA Reverse Transcription Kit Cat. No. 4366596)

| RT Mix Components | μL/rxn |
|---|---|
| 100 mM dNTP | 0.3 |
| 10x RT buffer | 1 |
| Rnase Inhibitor | 0.38 |
| Multiscribe RT enzyme | 1 |
| Water | 7.32 |

The RT cycling reaction is composed of 10 μL test sample, 10 μL of RT primer mix and 10 μL of RT Mix components for a total volume of 30 μL. The final concentration of the RT-primer in the total 30 μL total RT mix is 200 nM. The plate is then sealed with the same plate mat, briefly centrifuged at 800 rpm for 1 minute, then run on the thermocycler using the following cycling parameters:

| Cycling: | 16° C. | 30 minutes |
|---|---|---|
| | 42° C. | 30 minutes |
| | 85° C. | 5 minutes |
| | 4° C. | hold |

Next, 15 μL of Fast Enzyme/primer-probe mix is added to each well of a new Fast 96-well plate (Applied Biosystem's TaqMan Fast Universal PCR Master Mix, Cat. No. 4352042)

| ApoB PCR Master Mix Components | μL/rxn | Final Conc. |
|---|---|---|
| Fast Enyzme Mix (2x stock) | 10 | |
| forward primer (100 uM) | 0.18 | 900 nM |
| reverse primer (100 uM) | 0.18 | 900 nM |
| probe (10 uM) | 0.05 | 250 nM |
| Water | 4.59 | |

```
ApoB primers and probe sequence:
                                  (SEQ. ID. NO.: 12)
17063DC F3 GGCGCGAAATTTCAGGAATTGT (SEQ. ID. NO.: 13)
17063DC Pr2 CACTGGATACGACCTTTAACA (SEQ. ID. NO.: 14)
Universal R2 AGTGCAGGGTCCGAG
```

5 μL of each RT reaction is added to the Fast Enzyme Mix plate. The plate is centrifuged for 1 minute at 1000 rpm and the QPCR analysis is performed on an ABI7900 with Fast Block. Cycling parameters is: 1 cycle—95° C. for 20 seconds, followed by 40 Cycles—95° C. for 1 seconds, 60° C. for 20 seconds.

The QPCR result is utilized to calculate the siRNA concentration in the PEG antibody capture plate Triton lysates. Based on an estimate of 500 siRNA per LNP particle, the number of LNPs retained in each well of the anti-PEG antibody plate can be calculated. Using the ApoE concentration per well, as determined by the ApoE ELISA and the number of LNP particles per well, an approximate ApoE molecules bound per LNP particle can be calculated.

Example 3

Heparin Sepharose HI-TRAP™ Binding Assay

Lipid nanoparticles (LNP) with neutral surface charge are not retained after injection onto heparin sepharose with 1× Dulbecco's phosphate buffered saline (DPBS) as the running buffer but elute in the column void volume. Serum apolipoprotein E (ApoE) exhibits high affinity binding with heparin sulfate and it can be shown that LNPs bind to heparin sepharose to an extent dependent on their intrinsic ability to bind ApoE (depending on both lipid nanoparticle composition and ApoE concentration) after incubation with purified and/or recombinant human ApoE or serum samples. Lipid nanoparticles with surface bound ApoE bind to heparin sepharose with high affinity can be eluted only at high salt (1M NaCl).

A heparin sepharose binding assay is developed to assess serum ApoE binding to lipid nanoparticles based on the high affinity interaction that ApoE-LNP complexes exhibit toward heparin sepharose.

Incubations

Lipid nanoparticles are incubated at 37° C. for 20 min at a final siRNA concentration of 50 μg/mL with various concentrations of either purified or recombinant human apolipoprotein E or 0.1-50% rat/mouse/rhesus monkey/human serum in 1×Dulbecco's phosphate buffered saline (DPBS). After incubation with ApoE or serum LNP samples are diluted 10-fold using 1×DPBS and analyzed by heparin sepharose chromatography. Peak area of retained LNP (after subtraction of appropriate blank signals) is compared to total peak area of LNP control without ApoE and/or serum incubation to determine the percentage of the LNP which undergoes shift to high affinity heparin interaction after incubation with ApoE/serum.

Heparin Sepharose HI-TRAP™ Chromatographic Conditions

A heparin sepharose HI-TRAP™ chromatography column (GE Healthcare; 1 mL bed volume) is equilibrated with either 1× or 2× Dulbecco's PBS; the higher 2× salt concentration is used for LNPs with higher intrinsic retention on heparin sepharose (presumably due to higher positive surface charge).

Mobile Phase A: 1× or 2×DPBS
Mobile Phase B: 1M NaCl in 10 mM sodium phosphate buffer, pH 7.0
100% A delivered isocratically for 10 min followed by step gradient to 100% B; hold for additional 10 min; step gradient back to 100% A and reequilibrate for additional 10 min prior to injection of next sample
Flow rate: 1 mL/min
Sample injection volume: 50 μL.
Detection: UV @260 nm

Example 4

Rat In Vivo Evaluation of Efficacy and Toxicity

LNPs utilizing compounds in the nominal compositions described above, are evaluated for in vivo efficacy and increases in alanine amino transferase and aspartate amino transferase in Sprague-Dawley (Crl:CD(SD)) female rats (Charles River Labs). The siRNA targets the mRNA transcript for the ApoB gene (Accession # NM 019287). The primary sequence and chemical modification pattern of the ApoB siRNA is displayed above. The RDVs (containing siRNA) in PBS vehicle are tail vein injected in a volume of 1 to 1.5 mL. Infusion rate is approximately 3 ml/min. Five rats are used in each dosing group. After LNP administration, rats are placed in cages with normal diet and water present. Six hours post dose, food is removed from the cages. Animal necropsy is performed 24 hours after LNP dosing. Rats are anesthetized under isoflurane for 5 minutes, then maintained under anesthesia by placing them in nose cones continuing the delivery of isoflurane until ex-sanguination is completed. Blood is collected from the vena cava using a 23 gauge butterfly venipuncture set and aliquoted to serum separator vacutainers for serum chemistry analysis. Punches of the excised caudate liver lobe is taken and placed in RNALater (Ambion) for mRNA analysis. Preserved liver tissue is homogenized and total RNA isolated using a Qiagen bead mill and the Qiagen miRNA-Easy RNA isolation kit following the manufacturer's instructions. Liver ApoB mRNA levels are determined by quantitative RT-PCR. Message is amplified from purified RNA utilizing a rat ApoB commercial probe set (Applied Biosystems Cat # RN01499054_m1). The PCR reaction is performed on an ABI 7500 instrument with a 96-well Fast Block. The ApoB mRNA level is normalized to the housekeeping PPIB (NM 011149) mRNA. PPIB mRNA levels are determined by RT-PCR using a commercial probe set (Applied Biosytems Cat. No. Mm00478295_m1). Results are expressed as a ratio of ApoB mRNA/PPIB mRNA. All mRNA data is expressed relative to the PBS control dose. Serum ALT and AST analysis is performed on the Siemens Advia 1800 Clinical Chemistry Analyzer utilizing the Siemens alanine aminotransferase (Cat#03039631) and aspartate aminotransferase (Cat#03039631) reagents.

Example 5

Determination of Cationic Lipid Levels in Rat/Monkey Liver

Liver tissue is weighed into 20-ml vials and homogenized in 9 v/w of water using a GenoGrinder 2000 (OPS Diagnostics, 1600 strokes/min, 5 min). A 50 µL aliquot of each tissue homogenate is mixed with 300 µL of extraction/protein precipitating solvent (50/50 acetonitrile/methanol containing 500 nM internal standard) and the plate is centrifuged to sediment precipitated protein. A volume of 200 µL of each supernatant is then transferred to separate wells of a 96-well plate and 10 µl samples were directly analyzed by LC/MS-MS.

Standards are prepared by spiking known amounts of a methanol stock solution of compound into untreated rat liver homogenate (9 vol water/weight liver). Aliquots (50 µL) each standard/liver homogenate is mixed with 300 µL of extraction/protein precipitating solvent (50/50 acetonitrile/methanol containing 500 nM internal standard) and the plate is centrifuged to sediment precipitated protein. A volume of 200 µL of each supernatant is transferred to separate wells of a 96-well plate and 10 µl of each standard is directly analyzed by LC/MS-MS.

Absolute quantification versus standards prepared and extracted from liver homogenate is performed using an Aria LX-2 HPLC system (Thermo Scientific) coupled to an API 4000 triple quadrupole mass spectrometer (Applied Biosystems). For each run, a total of 10 µL sample is injected onto a BDS Hypersil C8 HPLC column (Thermo, 50×2 mm, 3 m) at ambient temperature.

Mobile Phase A:

95% H2O/5% methanol/10 mM ammonium formate/0.1% formic acid Mobile Phase B: 40% methanol/60% n-propanol/10 mM ammonium formate/0.1% formic acid The flow rate is 0.5 mL/min and gradient elution profile is as follows: hold at 80% A for 0.25 min, linear ramp to 100% B over 1.6 min, hold at 100% B for 2.5 min, then return and hold at 80% A for 1.75 min. Total run time is 5.8 min. API 4000 source parameters is CAD: 4, CUR: 15, GS1: 65, GS2: 35, IS: 4000, TEM: 550, CXP: 15, DP: 60, EP: 10.

Example 6

Rhesus Monkey In Vivo Evaluation of ApoB Efficacy

LNPs utilizing compounds in the nominal compositions described above, are evaluated for in vivo efficacy in male or female *Macaca mulatta* (rhesus) monkeys. The siRNA targets the mRNA transcript for the ApoB gene (Accession # XM 001097404). The primary sequence and chemical modification pattern of the ApoB siRNA is displayed above. The RDVs (containing siRNA) in PBS vehicle are administered by intravenous injection in the saphenous vein at an injection rate of 20 mL/minute to a dose level of 0.25 mg/kilogram siRNA. The injection volumes are from 1.9 to 2.1 mL/kilogram and monkeys can range in weight from 2.5 to 4.5 kilograms. The RDV or PBS control is administered to three monkeys. At multiple days post dose, 1 mL blood samples are drawn from the femoral artery for serum chemistry analysis. Monkeys are fasted overnight prior to blood draws. As a measure of efficacy, LDL-C is monitored as a downstream surrogate marker of ApoB mRNA reduction.

Example 7

Rhesus Monkey In Vivo Evaluation of β-Catenin Efficacy

On study day −7 predose liver biopsy samples (~0.5-1 gram/sample) are collected from male rhesus monkeys by laparoscopic surgical resection (resection of one biopsy sample from outer edge of one randomly selected liver lobe per monkey). A 5 mm tissue punch is used to sample three non-adjacent ~50 mg samples from each predose biopsy. Samples are preserved in RNAlater™ (Ambion) for later CTNNB1 mRNA analysis.

On study day 0 monkeys are administered suspensions of the lipid nanoparticle (LNP) test articles in phosphate buffered saline (0.05-0.1 mg siRNA/mL) via single-dose intravenous bolus injection at target doses of 0.67, 1.34 or 3.34 mg siRNA/m². For dosing purposes, body surface area (m²) is estimated from body weight according to the established allometric scaling relationship given below (1):

$$BSA\ (m^2) = 0.11 * BW\ (in\ kg)^{0.65}$$

On study days 2 and 7, at 48 hours and 168 hrs post LNP administration, liver biopsy samples (~0.5-1 gram/sample) are collected from monkeys by laparoscopic surgical resection (2 separate randomly selected liver lobes were resected per monkey). A 5 mm tissue punch is used to sample three non-adjacent ~50 mg samples per each 48 hr and 168 hr surgical biopsy sample. Samples are preserved in RNAlater™ (Ambion) for later CTNNB1 mRNA analysis.

CTNNB1 mRNA levels are measured by relative quantitative RT-PCR using a primer/probe set validated for CTNNB1 and normalized against mRNA levels of peptidyl-prolyl isomerase B (also known as PPIB or cyclophilin B) and RNA levels of 18S ribosomal RNA (18S rRNA). Change in CTNNB1 mRNA liver expression are measured as the difference in PCR threshold cycle number ($\Delta\Delta Ct$) between post-dose samples and each corresponding monkey's predose liver samples.

Calculation of CTNNB1 mRNA knockdown (with respect to pretreatment levels) is calculated from $\Delta\Delta Ct$ using the following relationship:

$$\text{mRNA}(\% \text{ knockdown}) = 100 - (100/2^{-\Delta\Delta Ct})$$

(1) FDA Guidance Document: "Guidance for Industry: Estimating the Maximum Safe Starting Dose in Initial Clinical Trials for Therapeutics in Adult Healthy Volunteers" July 2005, US Department of Health and Human Services, Food and Drug Administration—Center for Drug Evaluation and Research (CDER)

Example 8

Rhesus Monkey In Vivo Evaluation of ALT Increases

Alanine aminotransferase (ALT) is measured in serum that is harvested from clotted monkey whole blood after centrifugation. A Roche Modular System automated chemistry analyzer measures the enzymatic activity of ALT in the serum by using International Federation of Clinical Chemistry standardized procedures and reagents. The analyzer's computer uses absorbance measurements to calculated ALT activity in the sample as compared to a standard curve. The ALT activity is reported in International Units per Liter (IU/L).

What is claimed is:

1. A cationic lipid of Formula A:

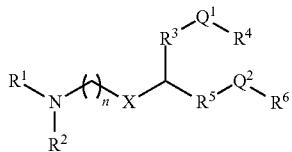

wherein:

$R^1$ and $R^2$ are each independently selected from the group consisting of H, $(C_1-C_6)$alkyl, heterocyclyl, and polyamine, wherein said alkyl, heterocyclyl and polyamine are optionally substituted with one to three R';

or $R^1$ and $R^2$ can be taken together with the nitrogen to which they are attached to form a monocyclic heterocycle with 4-7 members optionally containing, in addition to the nitrogen, one or two additional heteroatoms selected from N, O and S, said monocyclic heterocycle is optionally substituted with one to three R';

$R^3$ is selected from the group consisting of $(C_4-C_{20})$alkyl and $(C_4-C_{20})$alkenyl, said alkyl or alkenyl is optionally substituted with one to three R';

$R^4$ is selected from the group consisting of $(C_1-C_{16})$alkyl and $(C_2-C_{16})$alkenyl, said alkyl or alkenyl is optionally substituted with one to three R';

R⁵ is selected from the group consisting of $(C_4-C_8)$alkyl and $(C_4-C_8)$alkenyl, said alkyl or alkenyl is optionally substituted with one to three R';

R⁶ is $(C_1-C_2)$alkyl optionally substituted with one to three R';

$Q^1$ and $Q^2$ are each, independently, selected from the group consisting of a bond, —OC(O)—, —C(O)O—, —SC(O)—, —C(O)S—, —OC(S)—, —S—S—, —C(R")=N—, —N=C(R")—, —C(R")=N—O—, —O—N=C(R")—, —C(O)(NR")—, —N(R")C(O)—, C(S)(NR")—, —N(R")C(O)—, —N(R")C(O)N(R")—, —OC(O)O—, OSi(R")₂O—, —C(O)(CR"₂)C(O)O— and —OC(O)(CR"₂)C(O)—), with the proviso that when either $Q^1$ or $Q^2$ is a bond then the other is not a bond;

X is selected from the group consisting of —OC(O)—, —C(O)O—, —SC(O)—, —C(O)S—, —OC(S)—, —S—S—, —C(R")=N—, —N=C(R")—, —C(R")=N—O—, —O—N=C(R")—, —C(O)(NR")—, —N(R")C(O)—, C(S)(NR")—, —N(R")C(O)—, —N(R")C(O)N(R")—, —OC(O)O—, OSi(R")₂O—, —C(O)(CR"₂)C(O)O— and —OC(O)(CR"₂)C(O)—), each occurrence of R' is independently selected from the group consisting of halogen, R", OR", SR", CN, CO₂R" or CON(R")₂;

each occurrence of R" is independently selected from the group consisting of H and $(C_1-C_6)$alkyl, wherein said alkyl is optionally substituted with halogen and OH; and n is 1, 2, 3, 4 or 5;

or a pharmaceutically acceptable salt or stereoisomer thereof;

with the proviso that at least one of $R^3-Q^1-R^4$ or $R^5-Q^2-R^6$ is

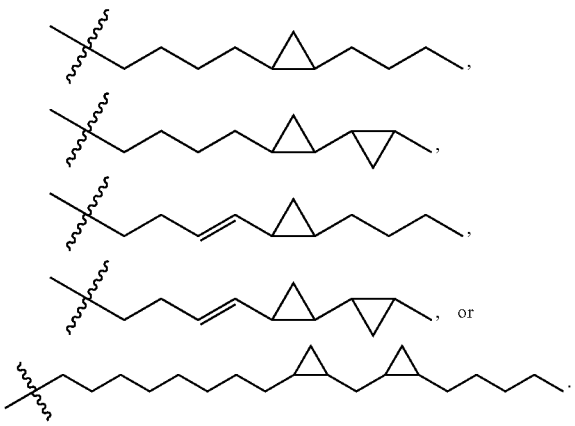

2. A cationic lipid of Formula A according to claim 1, wherein:

$R^1$ and $R^2$ are each methyl;

n is 3;

$R^3$ is selected from the group consisting of $(C_4-C_{20})$alkyl and $(C_4-C_{20})$alkenyl, said alkyl or alkenyl is optionally substituted with one to three R';

$R^4$ is selected from the group consisting of $(C_1-C_{16})$alkyl and $(C_2-C_{16})$alkenyl, said alkyl or alkenyl is optionally substituted with one to three R';

$R^5$ is selected from the group consisting of $(C_4-C_8)$alkyl and $(C_4-C_8)$alkenyl, said alkyl or alkenyl is optionally substituted with one to three R';

$R^6$ is $(C_1-C_2)$alkyl optionally substituted with one to three R';

$Q^1$ and $Q^2$ are each, independently, a bond or —C(O)O—, with the proviso that when either $Q^1$ or $Q^2$ is a bond then the other is not a bond; and X is —C(O)O—;

or a pharmaceutically acceptable salt or stereoisomer thereof;

with the proviso that at least one of $R^3-Q^1-R^4$ or $R^5-Q^2-R^6$ is

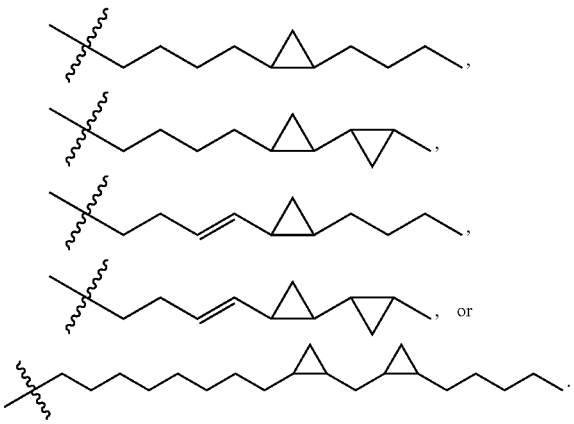

3. A lipid nanoparticle comprising a cationic lipid of claim 1.

4. The lipid nanoparticle of claim 3, wherein the lipid nanoparticle further comprises an oligonucleotide.

5. The lipid nanoparticle of claim 4, wherein the oligonucleotide is an siRNA or miRNA.

6. The lipid nanoparticle of claim 5, wherein the oligonucleotide is an siRNA.

7. The lipid nanoparticle of claim 3, wherein the lipid nanoparticle further comprises cholesterol and PEG-DMG.

8. The lipid nanoparticle of claim 3, wherein the lipid nanoparticle further comprises cholesterol, PEG-DMG and DSPC.

9. The lipid nanoparticle of claim 3, wherein the lipid nanoparticle further comprises cholesterol, PEG-C-DMA and DSPC.

* * * * *